United States Patent
Smith et al.

(10) Patent No.: US 10,344,006 B2
(45) Date of Patent: Jul. 9, 2019

(54) AMINE-CONTAINING ACYCLIC HYDROFLUOROETHERS AND METHODS OF USING THE SAME

(71) Applicant: 3M INNOVATIVE PROPERTIES COMPANY, St. Paul, MN (US)

(72) Inventors: Sean M. Smith, Woodbury, MN (US); Michael J. Bulinski, Stillwater, MN (US); Michael G. Costello, Afton, MN (US); William M. Lamanna, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 16/073,854

(22) PCT Filed: Feb. 22, 2017

(86) PCT No.: PCT/US2017/018780
§ 371 (c)(1),
(2) Date: Jul. 30, 2018

(87) PCT Pub. No.: WO2017/155686
PCT Pub. Date: Sep. 14, 2017

(65) Prior Publication Data
US 2019/0040024 A1     Feb. 7, 2019

Related U.S. Application Data

(60) Provisional application No. 62/306,947, filed on Mar. 11, 2016.

(51) Int. Cl.
| | |
|---|---|
| C07D 265/30 | (2006.01) |
| C07D 223/04 | (2006.01) |
| C07C 217/26 | (2006.01) |
| C07D 241/04 | (2006.01) |
| C07D 207/10 | (2006.01) |
| C07D 211/38 | (2006.01) |
| C11D 9/28 | (2006.01) |
| C11D 3/24 | (2006.01) |
| C11D 7/28 | (2006.01) |
| C09K 5/04 | (2006.01) |

(52) U.S. Cl.
CPC .......... C07D 265/30 (2013.01); C07C 217/26 (2013.01); C07D 207/10 (2013.01); C07D 211/38 (2013.01); C07D 223/04 (2013.01); C07D 241/04 (2013.01); C09K 5/04 (2013.01); C11D 3/245 (2013.01); C11D 7/28 (2013.01); C11D 9/28 (2013.01)

(58) Field of Classification Search
CPC .. C07D 265/30; C07D 207/10; C07D 211/38; C07D 223/04; C07D 241/04; C07C 217/26; C09K 5/04; C11D 3/245; C11D 7/28; C11D 9/28
See application file for complete search history.

(56) References Cited

U.S. PATENT DOCUMENTS

| | | | |
|---|---|---|---|
| 3,700,695 A | 10/1972 | Carr | |
| 4,736,045 A | 4/1988 | Drakesmith | |
| 4,782,148 A | 11/1988 | Abe | |
| 4,985,556 A | 1/1991 | Abe | |
| 5,049,670 A | 9/1991 | Moore | |
| 6,024,176 A * | 2/2000 | Moore | A61K 9/0026 169/46 |
| 6,149,980 A * | 11/2000 | Behr | C07C 43/123 427/384 |
| 6,291,417 B1 * | 9/2001 | Flynn | C07C 43/12 134/40 |
| 6,548,471 B2 * | 4/2003 | Flynn | C07C 43/12 134/40 |
| 7,988,877 B2 * | 8/2011 | Flynn | C07C 41/16 252/2 |
| 8,193,397 B2 * | 6/2012 | Flynn | B23K 35/3612 237/81 |
| 8,261,560 B2 * | 9/2012 | Flynn | C09K 5/10 165/104.19 |

(Continued)

FOREIGN PATENT DOCUMENTS

| | | |
|---|---|---|
| CN | 104577200 | 4/2015 |
| JP | 01070445 | 3/1989 |

(Continued)

OTHER PUBLICATIONS

Abe, "A New Route to Perfluorovinylamines by the Pyrolytic Reaction of an Alkali Metal Salt of Perfluoro (2-Dialkylamino-Propionic Acids)", Chemistry Letters, 1988, pp. 1887-1890.

(Continued)

*Primary Examiner* — Alexander R Pagano
(74) *Attorney, Agent, or Firm* — Julie Lapos-Kuchar

(57) ABSTRACT

An acyclic fluorinated compound of formula (I) is amine-containing acyclic hydrofluoroethers. The acyclic fluorinated compound is useful as heat transfer, solvent cleaning, fire extinguishing agents and electrolyte solvents and additives.

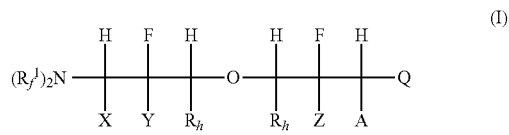

17 Claims, No Drawings

(56) References Cited

U.S. PATENT DOCUMENTS

| | | | | |
|---|---|---|---|---|
| 8,350,094 | B2* | 1/2013 | Flynn | C07C 41/16 252/2 |
| 8,535,559 | B2* | 9/2013 | Flynn | B23K 35/0244 252/73 |
| 8,633,288 | B2 | 1/2014 | Dams | |
| 9,540,316 | B2* | 1/2017 | Bulinski | C07C 217/46 |
| 10,030,185 | B2* | 7/2018 | Bulinski | C09K 5/04 |
| 2010/0104950 | A1 | 4/2010 | Lamanna | |
| 2010/0137609 | A1 | 6/2010 | Iwaya | |

FOREIGN PATENT DOCUMENTS

| | | |
|---|---|---|
| WO | WO 2008-070606 | 6/2008 |
| WO | WO 2010-074327 | 7/2010 |
| WO | WO 2016-048808 | 3/2016 |
| WO | WO 2016-094113 | 6/2016 |
| WO | WO 2017-155686 | 9/2017 |
| WO | WO 2017-155735 | 9/2017 |

OTHER PUBLICATIONS

Abe, "An Alternative New Route to Perfluorovinylamines. Pyrolysis of an Alkali Metal Salt of Perfluoro (3-dialkylamino-propionic acids)", Chemistry Letters, 1989, pp. 905-908.

Abe, "The Electrochemical Fluorination of Nitrogen-Containing Carboxylic Acids. Fluorination of Dimethylamino- or Diethylamino-Substituted Carboxylic Acid Derivatives", Journal of Fluorine Chemistry, 1990, vol. 48, pp. 257-279.

Abe, "The Electrochemical Fluorination of Nitrogen-Containing Carboxylic Acids. Fluorination of Methyl Esters of Cyclic Amino Group Substituted Carboxylic Acids", Journal of Fluorine Chemistry, 1990, vol. 50, pp. 173-196.

Chambers, "Free Radical Chemistry. Part 3.[1] Substituent Effects in Additions of Ethers to Fluorinated Alkenes", Journal of the Chemical Society, Perkin Transactions, 1985, pp. 2209-2213.

Chambers, "Free Radical Chemistry. Part 4.[1] Stereoelectronic Effects in the Additions of Cyclic Ethers to Fluorinated Alkenes", Journal of the Chemical Society, Perkin Transactions, 1985, pp. 2215-2218.

Chambers, "Free-Radical Chemistry. Part 5 [1]. A New Approach to the Synthesis of Perfluorinated Ethers", Journal of Fluorine Chemistry, 1985, vol. 29, pp. 323-339.

Chambers, "Free-Radical Chemistry. Part 8 [1]. Electrochemical Fluorination of Partly Fluorinated Ethers", Journal of Fluorine Chemistry, 1990, vol. 49, pp. 409-419.

Chen, "Synthesis of Cyclic Ethers with Fluorinated Side Chains", Inorganic Chemistry, 1996, vol. 35, pp. 1590-1601.

Chi, "A Facile Synthesis of Partly-Fluorinated Organic Compounds Using Perfluoropropoxyethylene and Amines", Bulletin of the Korean Chemical Society, 1999, vol. 20, No. 5, pp. 499-502.

Ellis, "Cleaning and Contamination of Electronics Components and Assemblies", Electrochemical Publications Limited, 1986, pp. 182-194.

Paleta, "Radical Additions to Fluoro-Olefins. Photochemical Mono-Fluoroalkylation and Sequential Bis-Fluoroalkylation of Oxolane", Journal of Fluorine Chemistry, 1996, vol. 80, pp. 125-134.

International Search Report for PCT International Application No. PCT/US2017/018780, dated May 29, 2017, 4 pages.

* cited by examiner

AMINE-CONTAINING ACYCLIC HYDROFLUOROETHERS AND METHODS OF USING THE SAME

CROSS REFERENCE TO RELATED APPLICATIONS

This application is a national stage filing under 35 U.S.C. 371 of PCT/US2017/018780, filed Feb. 22, 2017, which claims the benefit of U.S. Application No. 62/306947, filed Mar. 11, 2016, the disclosure of which is incorporated by reference in its/their entirety herein.

TECHNICAL FIELD

The present disclosure relates to amine-containing acyclic hydrofluoroethers and methods of using the same.

SUMMARY

There continues to be a need for inert fluorinated fluids which have low global warming potential while providing high thermal stability, low toxicity, nonflammability, good solvency, and a wide operating temperature range to meet the requirements of various applications. Those applications include, but are not restricted to, heat transfer, solvent cleaning, fire extinguishing agents, and electrolyte solvents and additives.

In one aspect, an acyclic fluorinated compound of the general formula (I) is disclosed

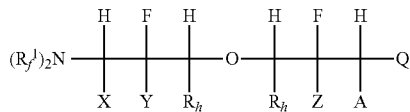

where:

X is selected from F or $CF_3$, and Y is selected from H, F or $CF_3$, wherein when X is $CF_3$ then Y is F and when Y is $CF_3$ then X is F;

each $R_f^1$ is independently selected from a linear or branched perfluorinated alkyl group comprising 1-8 carbon atoms and optionally comprising at least one catenated atom selected from O, N, or combinations thereof; or the two $R_f^1$ groups are bonded together to form a fluorinated ring structure comprising 4-8 carbon atoms and optionally comprising at least one catenated atom selected from O, N, or combinations thereof;

each $R_h$ is independently H or $CH_3$;

A is selected from F or $CF_3$;

Z is selected from H, F, or $CF_3$ and

Q is selected from (i) a F atom, (ii) a Cl atom, (iii) a linear, cyclic, or branched perfluorinated alkyl group comprising 1-8 carbon atoms and optionally comprising at least one catenated atom selected from O, N, or combinations thereof, or (iv) a $G(R_f^2)_e$ group, where G is an O atom or a N atom wherein:

when Q is a Cl atom, then Z and A are F atoms;

when G is O then e is 1, Z is H, F, or $CF_3$; A is F; and $R_f^2$ is a linear or branched perfluorinated alkyl group comprising 1-10 carbon atoms and optionally comprising at least one catenated atom selected from O, N, or combinations thereof;

when G is N then e is 2, and each $R_f^2$ group is independently a linear or branched perfluorinated alkyl group comprising 1-8 carbon atoms and optionally comprising at least one catenated atom selected from O, N, or combinations thereof or the two $R_f^2$ groups are bonded together to form a fluorinated ring structure comprising 4-8 carbon atoms and optionally comprising at least one catenated atom selected from O, N, or combinations thereof with the proviso that when A is $CF_3$ then Z is F, and when Z is $CF_3$ then A is F.

The above summary is not intended to describe each embodiment. The details of one or more embodiments of the invention are also set forth in the description below. Other features, objects, and advantages will be apparent from the description and from the claims.

DETAILED DESCRIPTION

As used herein, the term

"a", "an", and "the" are used interchangeably and mean one or more; and

"and/or" is used to indicate one or both stated cases may occur, for example A and/or B includes, (A and B) and (A or B);

"alkyl" refers to a monovalent group that is a radical of an alkane, which is a saturated hydrocarbon. The alkyl group can be linear, branched, cyclic or combinations thereof;

"catenated" means an atom other than carbon (for example, oxygen or nitrogen) that is bonded to at least two carbon atoms in a carbon chain (linear or branched or within a ring) so as to form a carbon-heteroatom-carbon linkage; and "perfluorinated" means a group or a compound wherein all hydrogen atoms in the C—H bonds have been replaced by C—F bonds.

As used herein, a chemical structure that depicts the letter "F" in the center of a ring indicates that all unmarked bonds of the ring are fluorine atoms.

Also herein, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 4, at least 6, at least 8, at least 10, at least 25, at least 50, at least 100, etc.).

Heat transfer fluids may be used to transmit heat from one location to another, for example, to prevent over heating of a device or to maintain precise temperature control or for energy conversion, as in the capture of waste heat and the conversion to electrical or mechanical energy. Presently, various fluids are used for heat transfer. The suitability of the heat transfer fluid depends upon the application process. For example, in some electronic applications, a heat-transfer fluid which is inert, has low toxicity, good environmental properties, and good heat transfer properties over a wide temperature range is desirable.

Vapor phase soldering is a process application that requires heat transfer fluids which are especially suitable for high temperature exposure. In such application, temperatures of between 170° C. and 250° C. are typically used with 200° C. being particularly useful for soldering applications using a lead based solder and 230° C. useful for the higher melting lead free solders. Currently, the heat transfer fluids used in this application are of the perfluoropolyether (PFPE) class. While many PFPEs have adequate thermal stability at the temperatures employed, they also possess the notable drawback of being environmentally persistent with extremely long atmospheric lifetimes which, in turn, gives rise to high global warming potentials (GWPs). As such, there is a need for new materials which possess the characteristics of the PFPEs that make them useful in vapor phase soldering as well as in other high temperature heat transfer applications (e.g., chemical inertness, thermal stability and effective heat transfer, liquid over a wide temperature range, good heat-transfer properties over a wide range of temperatures), but which have a much shorter atmospheric lifetime and lower GWPs.

In some embodiments, the acyclic fluorinated compound of the present disclosure may exhibit properties that render them particularly useful as heat transfer fluids for the electronics industry. For example, the acyclic fluorinated compound may be chemically inert (i.e., they do not easily react with base, acid, water, etc.), and may have high boiling points (up to 300° C.), low freezing points (the acyclic fluorinated compound may be liquid at −40° C. or lower), low viscosity, high thermal stability, good thermal conductivity, adequate solvency for a range of potentially important solutes, and low toxicity. The acyclic fluorinated compound of the present disclosure may also, surprisingly, be liquid at room temperature (e.g., between 20 and 25° C.).

Further, in one embodiment, the compounds of the present disclosure can be readily prepared in high yield via low cost starting materials. The starting materials can be readily purchased or derived from electrochemical fluorination. Thus, the compounds described in the present disclosure represent a new class of useful and potentially low cost fluorinated fluids that offer potential advantages in a variety of applications including heat transfer, cleaning, and electrolyte applications.

The acyclic fluorinated compound of the present disclosure (herein referred to interchangeably as a compound of the present disclosure) are of the general formula (I)

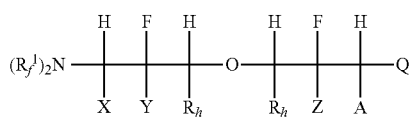

where:

X is selected from F or $CF_3$, and Y is selected from H, F, or $CF_3$, wherein (a) both X and Y are F, (b) X is $CF_3$ then Y is F, or (c) when Y is $CF_3$ then X is F;

each $R_f^1$ is independently selected from a linear or branched perfluorinated alkyl group comprising 1-8 carbon atoms and optionally comprising at least one catenated atom selected from O, N, or combinations thereof; or the two $R_f^1$ groups are bonded together to form a fluorinated ring structure comprising 4-8 carbon atoms and optionally comprising at least one catenated atom selected from O, N, or combinations thereof;

each $R_h$ is independently H or $CH_3$;

A is selected from F, or $CF_3$ and Z is selected from H, F or $CF_3$; and

Q is selected from a F atom, a Cl atom, a linear, cyclic, or branched perfluorinated alkyl group comprising 1-8 carbon atoms and optionally comprising at least one catenated atom selected from O, N, or combinations thereof, or a $G(R_f^2)_e$ group, where G is an O atom or a N atom wherein:

when Q is a Cl atom, then Z and A are F atoms;

when G is O then e is 1, Z is H, F, or $CF_3$; A is F; and $R_f^2$ is a linear or branched perfluorinated alkyl group comprising 1-10 carbon atoms and optionally comprising at least one catenated atom selected from O, N, or combinations thereof;

when G is N then e is 2, and each $R_f^2$ group is independently a linear or branched perfluorinated alkyl group comprising 1-8 carbon atoms and optionally comprising at least one catenated atom selected from O, N, or combinations thereof; or the two $R_f^2$ groups are bonded together to form a fluorinated ring structure comprising 4-8 carbon atoms and optionally comprising at least one catenated atom selected from O, N, or combinations thereof with the proviso that when A is $CF_3$ then Z is F, and when Z is $CF_3$ then A is F.

As used herein, an acyclic ether refers to a compound, wherein the ether oxygen atom is not contained within a cyclic ring, thus the oxygen atom shown in Formula (I) above is an acyclic ether.

In one embodiment, Q is linear, cyclic, or branched perfluorinated alkyl group comprising 1, 2, 3, 4, 5, 6, 7, or 8 carbon atoms and optionally comprising at least one catenated atom selected from O, N, or combinations thereof. In one embodiment, Q is also $N(R_f^1)_2$.

In one embodiment, Q comprises a perfluorinated morpholine group (i.e., 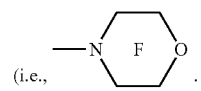).

Disclosed herein are exemplary compounds of the present disclosure.

In one embodiment, the amine-containing acyclic hydrofluoroethers of the present disclosure comprise a substituted diethyl ether. Such amine-containing acyclic hydrofluoroethers include:

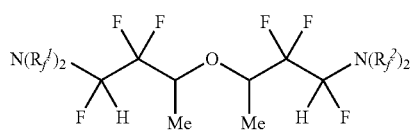

where $(R_f^1)_2N$ and $(R_f^2)_2N$ are independently selected from:

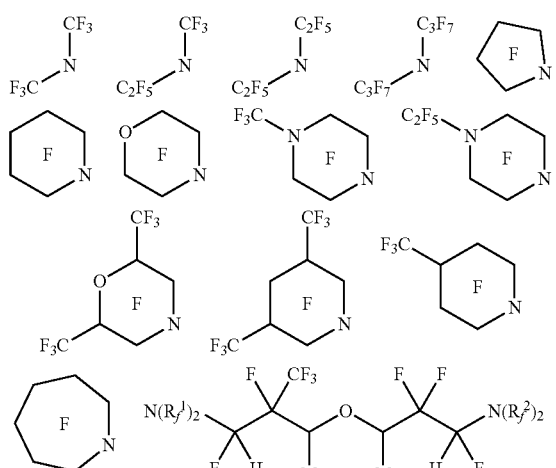

where $(R_f^1)_2N$ and $(R_f^2)_2N$ are independently selected from:

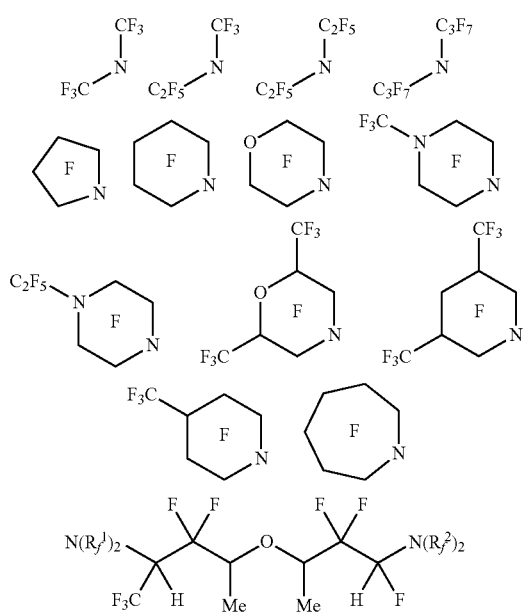
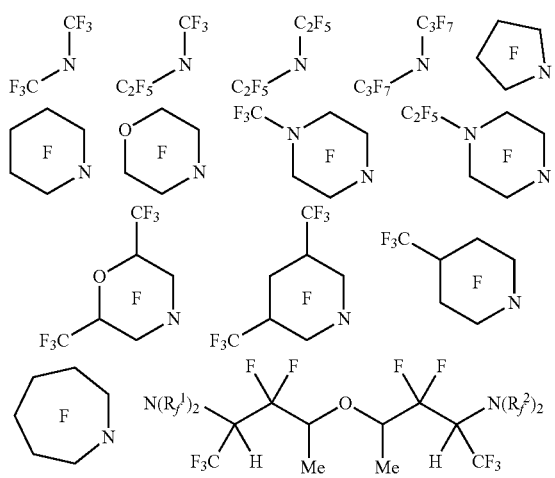
where $(R_f^1)_2N$ and $(R_f^2)_2N$ are independently selected from:
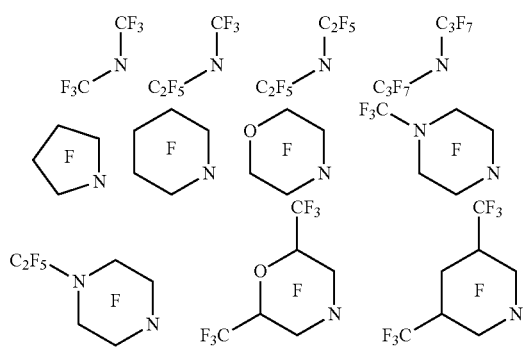
-continued
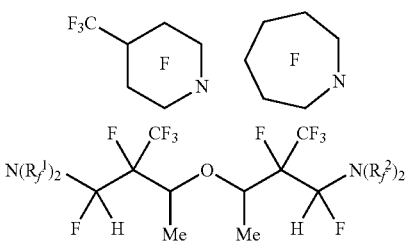
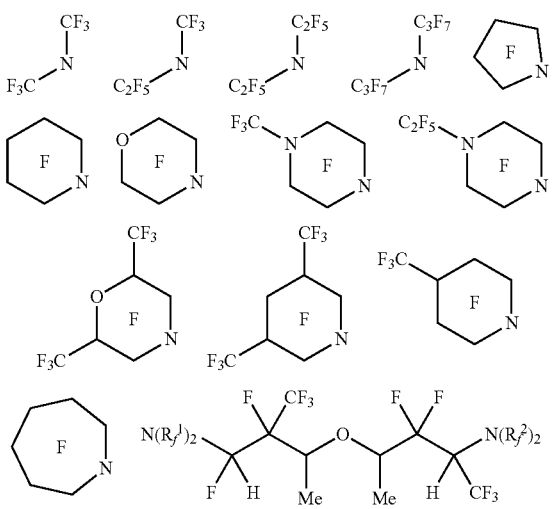
where $(R_f^1)_2N$ and $(R_f^2)_2N$ are independently selected from:
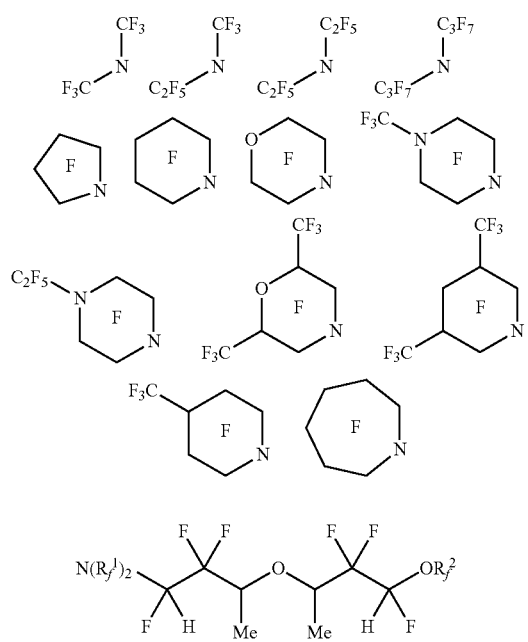

wherein $(R_f^1)_2N$ is selected from:

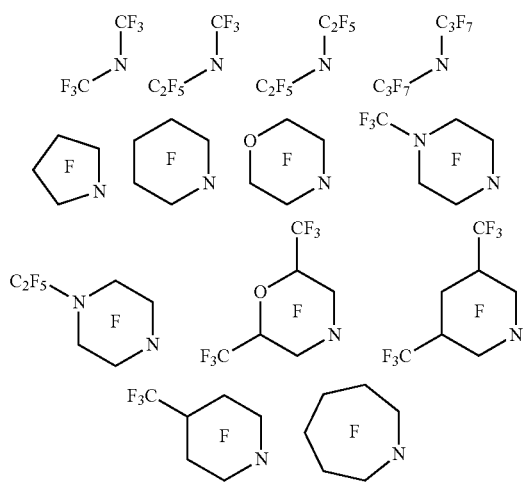

wherein $OR_f^2$ is selected from:

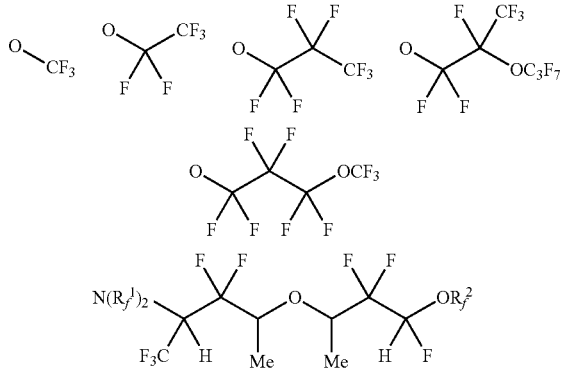

wherein $(R_f^1)_2N$ is selected from:

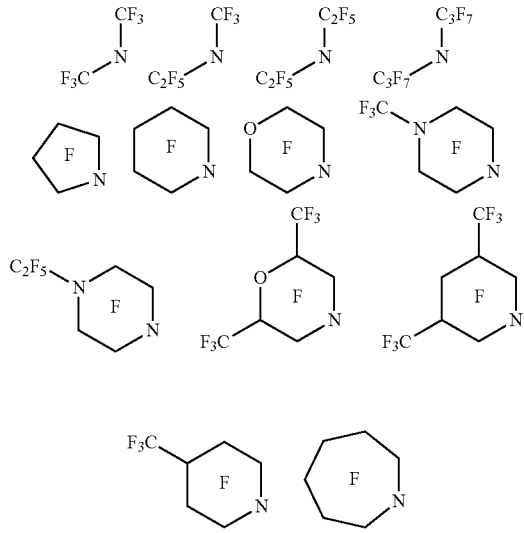

wherein $OR_f^2$ is selected from:

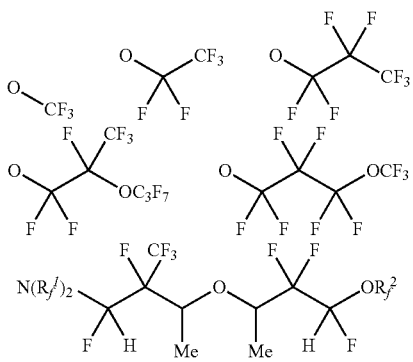

wherein $(R_f^1)_2N$ is selected from:

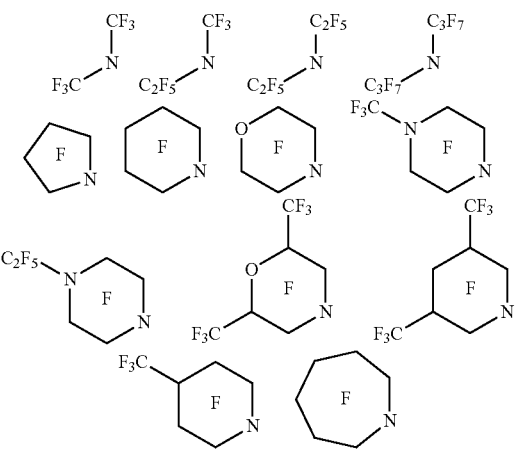

wherein $OR_f^2$ is selected from:

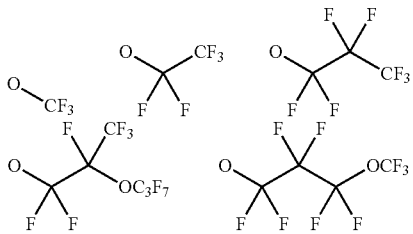

In one embodiment, the amine-containing acyclic hydrofluoroethers of the present disclosure comprise a substituted dimethyl ether. Such amine-containing acyclic hydrofluoroethers include:

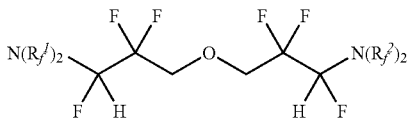

wherein $(R_f^1)_2N$ and $(R_f^2)_2N$ are independently selected from:

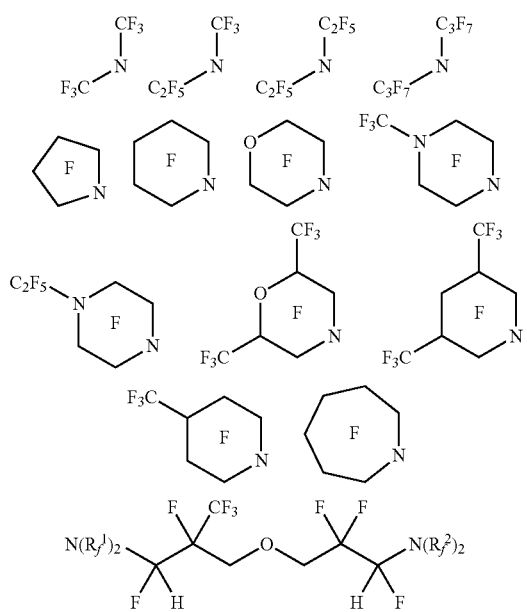
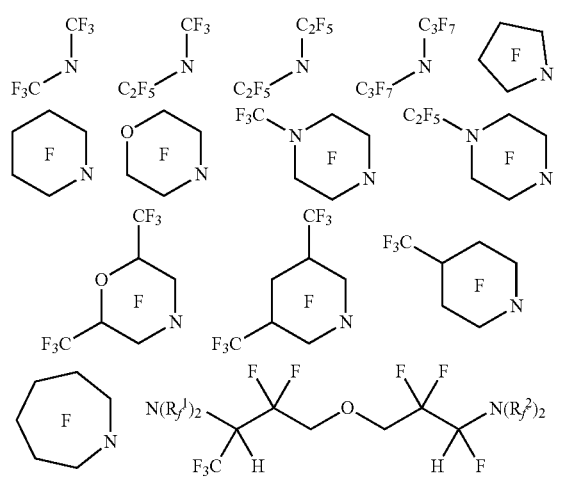
wherein $(R_f^1)_2N$ and $(R_f^2)_2N$ are independently selected from:
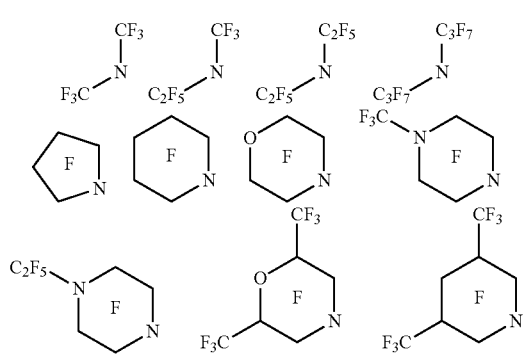
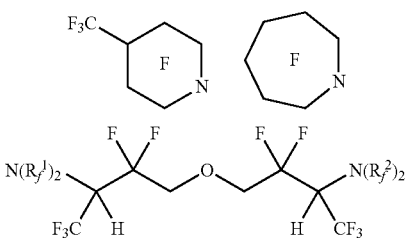
wherein $(R_f^1)_2N$ and $(R_f^2)_2N$ are independently selected from:
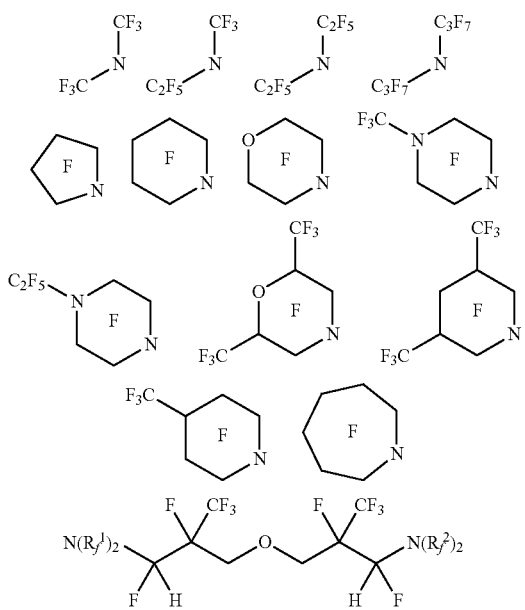
wherein $(R_f^1)_2N$ and $(R_f^2)_2N$ are independently selected from:
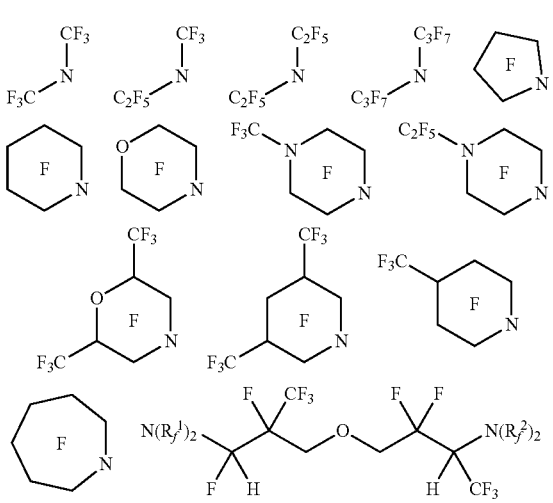
wherein $(R_f^1)_2N$ and $(R_f^2)_2N$ are independently selected from:

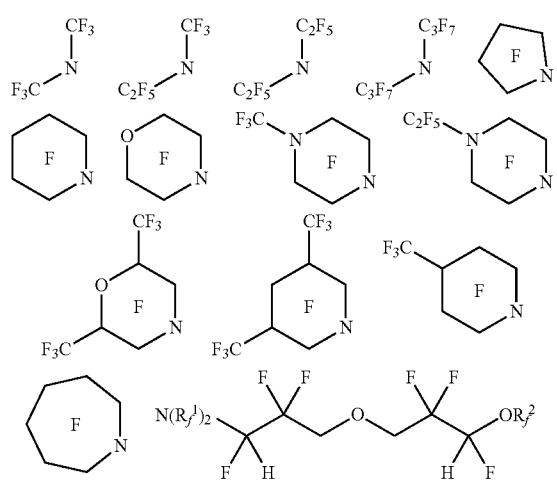
wherein $(R_f^1)_2N$ is selected from:
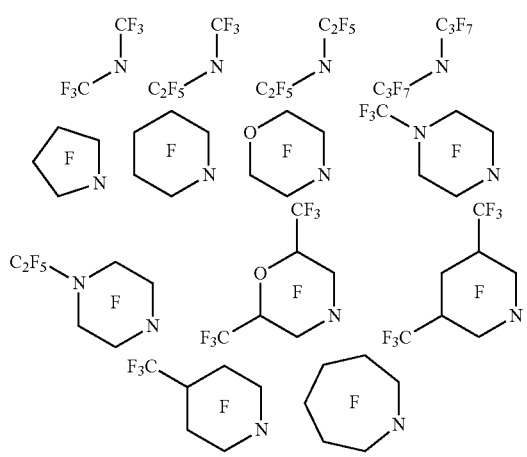
wherein $OR_f^2$ is selected from:
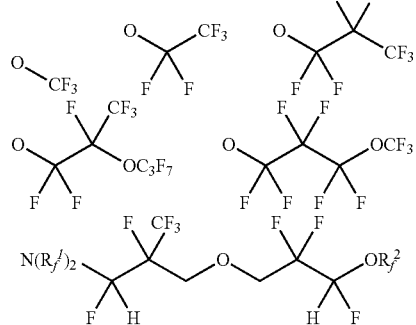
wherein $(R_f^1)_2N$ is selected from:
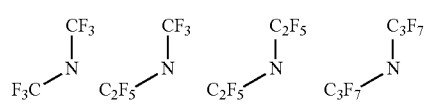
-continued
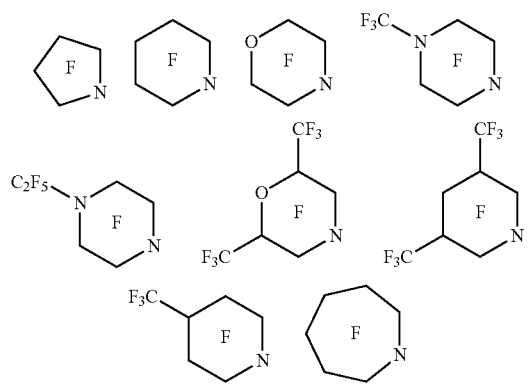
wherein $OR_f^2$ is selected from:
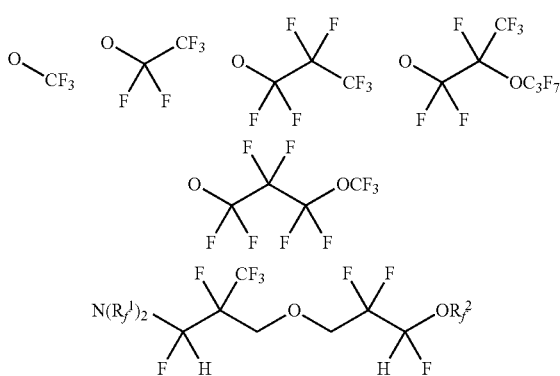
wherein $(R_f^1)_2N$ is selected from:
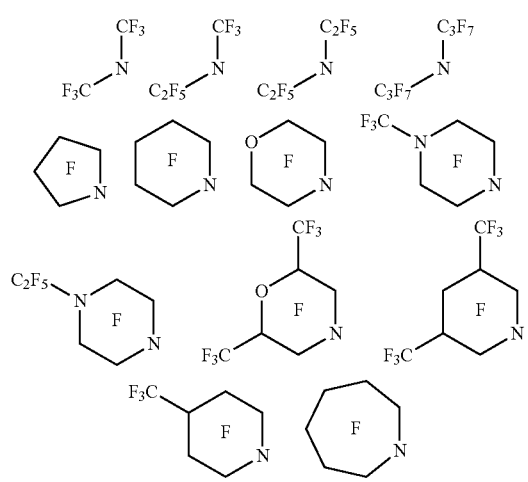
wherein $OR_f^2$ is selected from:
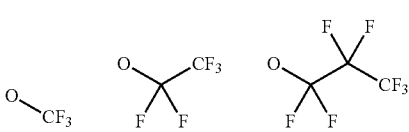

-continued
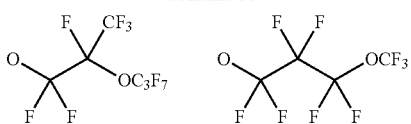
Exemplary amine-containing acyclic hydrofluoroethers include:
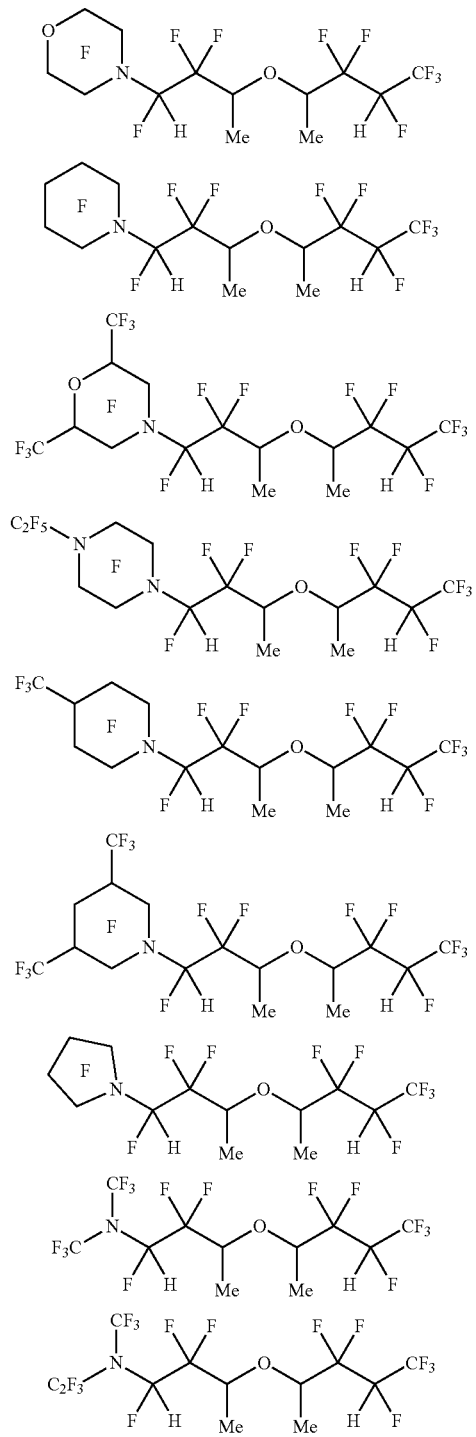
-continued
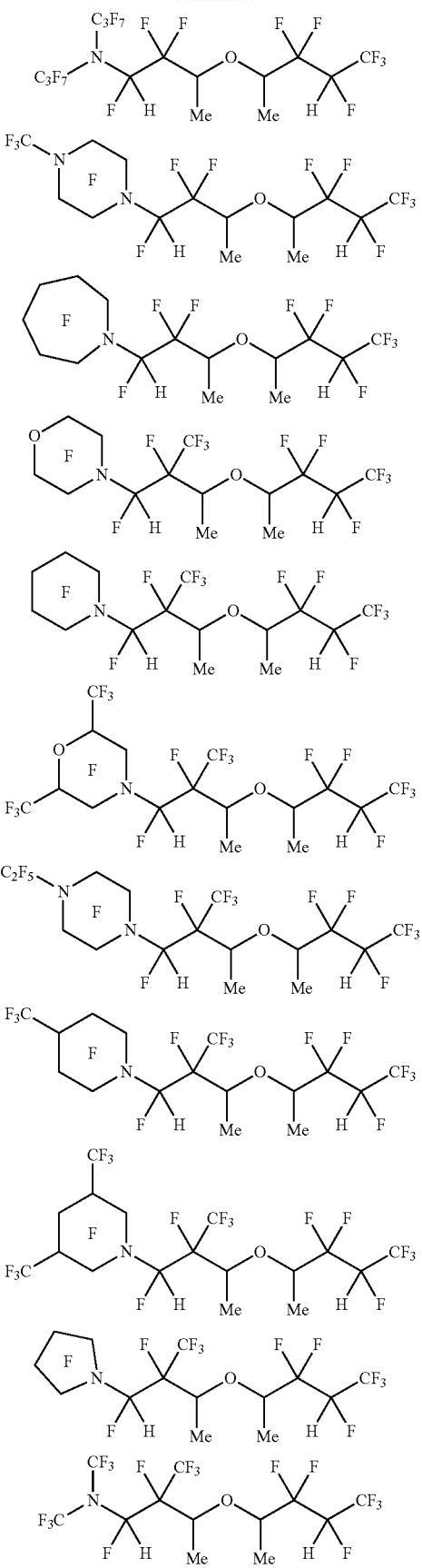

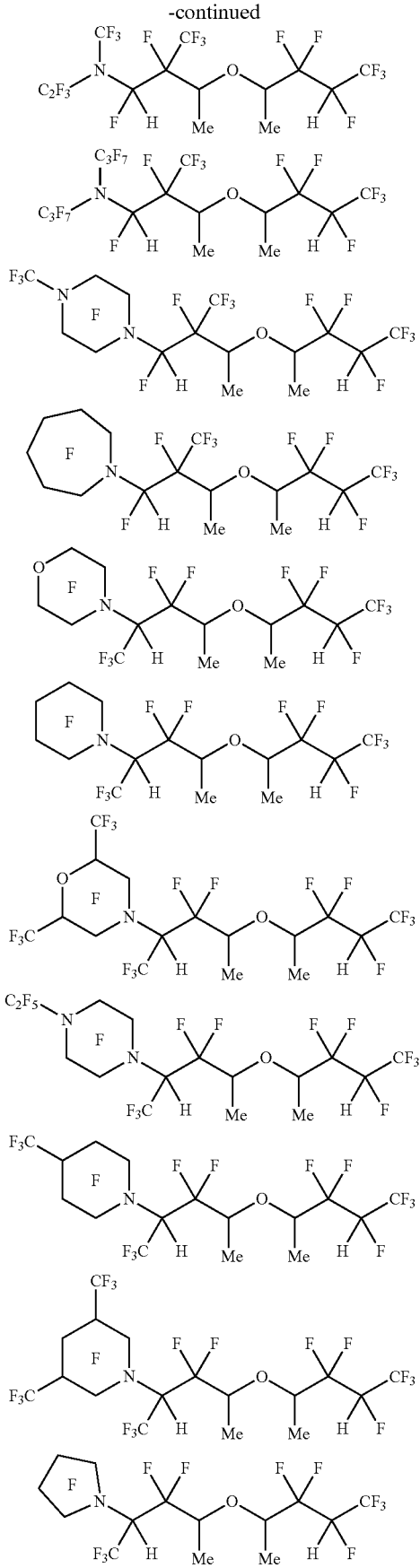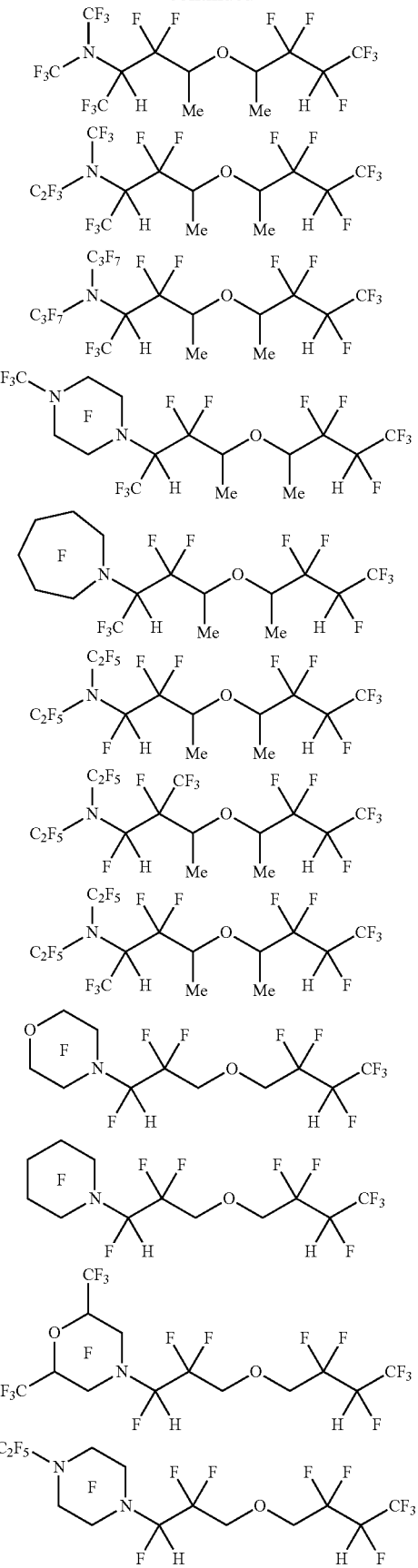

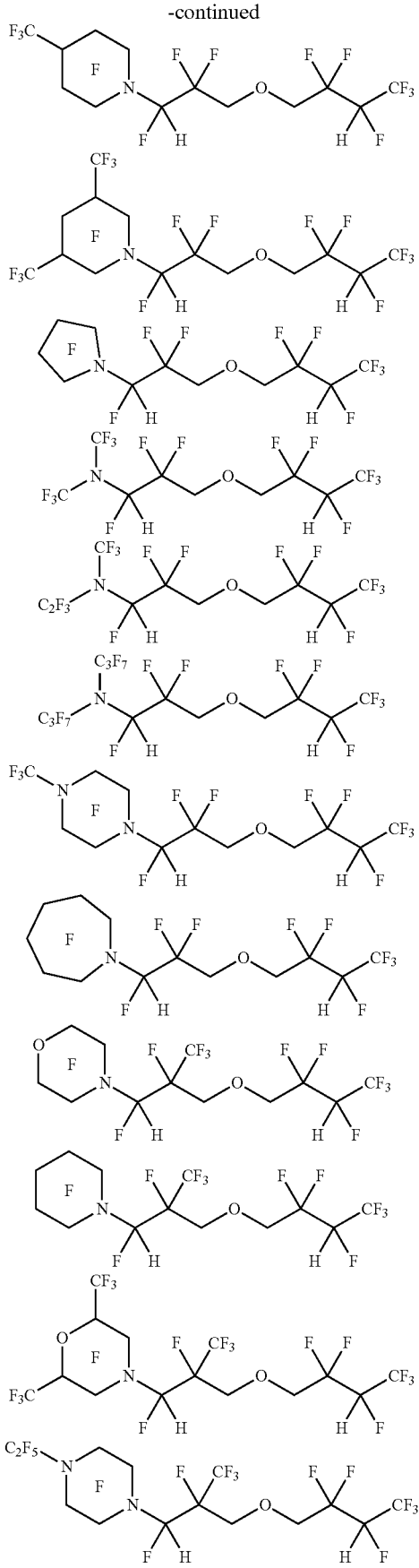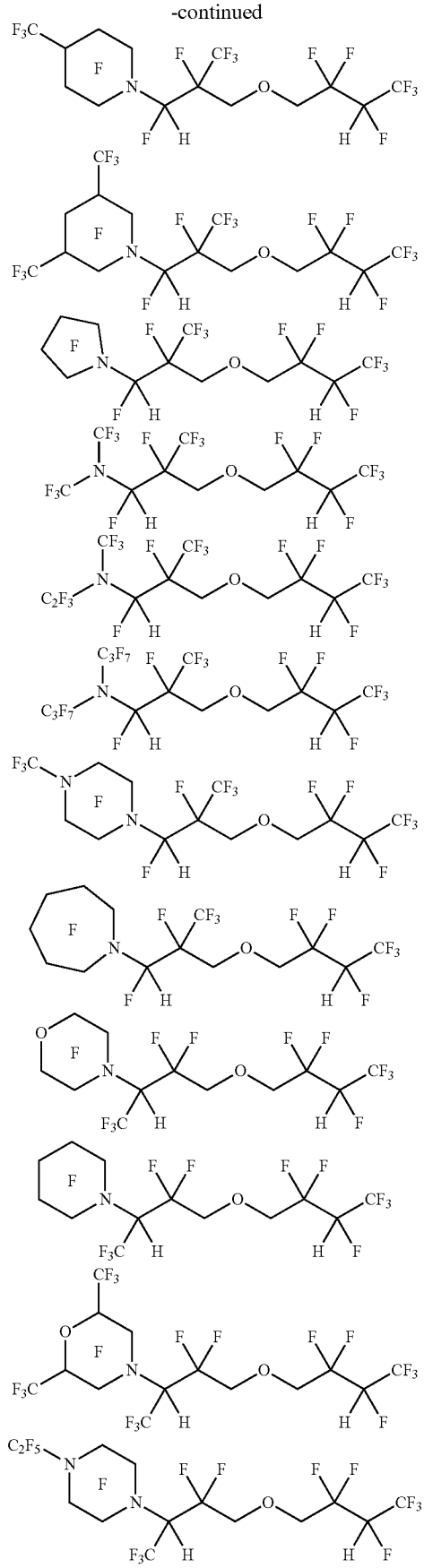

-continued

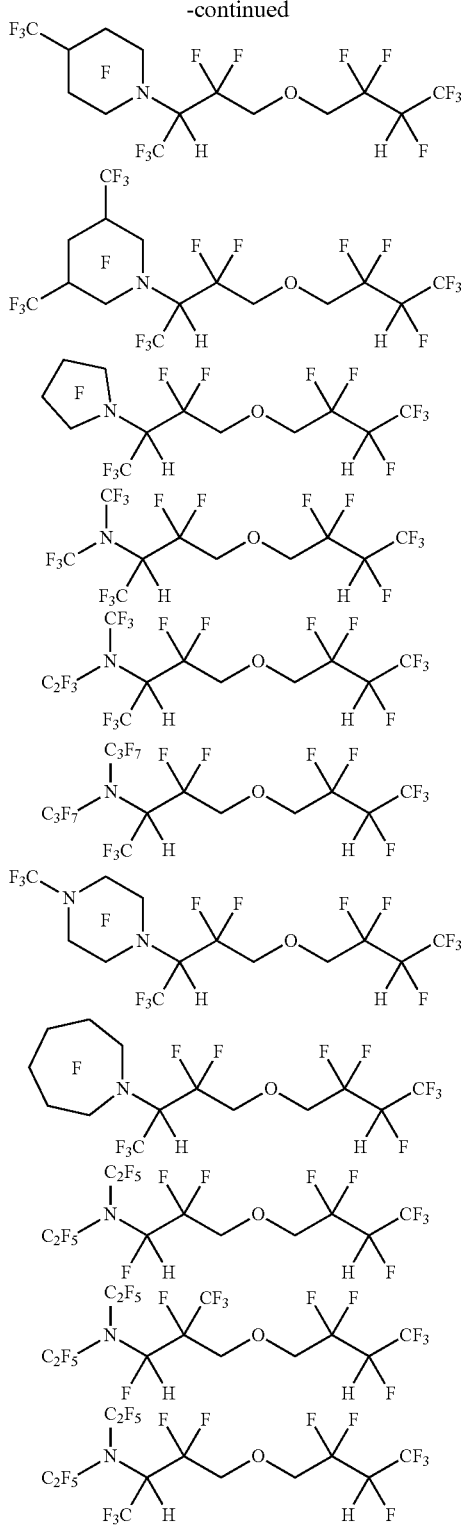

where "Me" refers to a methyl (—CH$_3$) group.

The compounds of the present disclosure have good environmental properties as well as having good performance attributes, such as non-flammability, chemical inertness, high thermal stability, good solvency, etc.

In one embodiment, the compound of the present disclosure may have a low environmental impact. In this regard, the compounds of the present disclosure may have a global warming potential (GWP) of less than 100, 50, or even 10. As used herein, GWP is a relative measure of the global warming potential of a compound based on the structure of the compound. The GWP of a compound, as defined by the Intergovernmental Panel on Climate Change (IPCC) in 1990 and updated in 2007, is calculated as the warming due to the release of 1 kilogram of a compound relative to the warming due to the release of 1 kilogram of CO$_2$ over a specified integration time horizon (ITH).

$$GWP_i(t') = \frac{\int_0^{ITH} a_i[C(t)]dt}{\int_0^{ITH} a_{CO_2}[C_{CO_2}(t)]dt} = \frac{\int_0^{ITH} a_i C_{oi} e^{-t/\tau_i} dt}{\int_0^{ITH} a_{CO_2}[C_{CO_2}(t)]dt}$$

In this equation $a_i$ is the radiative forcing per unit mass increase of a compound in the atmosphere (the change in the flux of radiation through the atmosphere due to the IR absorbance of that compound), C is the atmospheric concentration of a compound, $\tau$ is the atmospheric lifetime of a compound, t is time, and i is the compound of interest. The commonly accepted ITH is 100 years representing a compromise between short-term effects (20 years) and longer-term effects (500 years or longer). The concentration of an organic compound, i, in the atmosphere is assumed to follow pseudo first order kinetics (i.e., exponential decay). The concentration of CO$_2$ over that same time interval incorporates a more complex model for the exchange and removal of CO$_2$ from the atmosphere (the Bern carbon cycle model).

In one embodiment, the compounds of the present disclosure have atmospheric lifetime of less than 1 year, 0.5 years, or even less than 0.1 years.

Non-flammability can be assessed by using standard methods such as ASTM D-3278-96 e-1, D56-05 "Standard Test Method for Flash Point of Liquids by Small Scale Closed-Cup Apparatus". In one embodiment, the compound of the present disclosure is non-flammable based on closed-cup flashpoint testing following ASTM D-327-96 e-1.

In one embodiment, the compound of the present disclosure is non-bioaccumulative in animal tissues. For example, some compounds of the present disclosure may provide low log $K_{ow}$ values, indicating a reduced tendency to bioaccumulate in animal tissues, where $K_{ow}$ is the octanol/water partition coefficient, which is defined as the ratio of the given compound's concentration in a two-phase system comprising an octanol phase and an aqueous phase. In one embodiment, the log $K_{ow}$ value is less than 7, 6, 5, or even 4.

In one embodiment, the compound of the present disclosure is expected to provide low acute toxicity based on 4 hour acute inhalation or oral toxicity studies in rats following U.S. EPA "Health Effects Test Guidelines OPPTS 870.1100 Acute Oral Toxicity" and/or OECD Test No. 436 "Acute Inhalation Toxicity-Acute Toxic Class Method". For example, a compound of the present disclosure has a single dose oral median lethal dose (LD 50) in male and female Sprague-Dawley rats of greater than 30, 50, 100, 200, or even 300 mg/kg.

The useful liquid range of a compound of the present disclosure is between its pour point and its boiling point. A pour point is the lowest temperature at which the compound is still able to be poured. The pour point can be determined, for example, by ASTM D 97-16 "Standard Test Method for Pour Point of Petroleum Products". In one embodiment, the compound of the present disclosure has a pour point of less than 0° C., −20° C., −40° C. or even −60° C. In one embodiment, the compound of the present disclosure has a boiling point of at least 100° C., 150° C., 200° C., 250° C. or even 300° C.

In some embodiments, the compound of the present disclosure may be hydrophobic, relatively chemically unreactive, and thermally stable.

In some embodiments, the compound of the present disclosure may be prepared by free radical addition of acyclic ethers to fluorinated olefins, a chemistry which has been described by Chambers et al. in *J. Chem. Soc. Perkin Trans* 1, 1985, p. 2215-2218.

The acyclic fluorinated compound of formula (I) may be prepared from a linear or branched acyclic ether and an amine-containing fluorinated olefin as described below.

In one embodiment, the acyclic ethers are selected from: dimethyl ether, methyl ethyl ether, diethyl ether, cyclopentyl methyl ether, and isopropyl methyl ether. The fluorinated olefin comprises a terminal or internal double bond and at least one olefinic C—F bond. In one embodiment, the fluorinated olefin is perfluorinated. Exemplary amine-containing fluorinated olefins include: fluorinated vinyl amine and fluorinated 1- and 2-propenyl amines.

Fluorinated vinyl amine and fluorinated propenyl amine compounds can be prepared by electrochemical perfluorination of the appropriate nitrogen-containing hydrocarbon carboxylate derivatives followed by decarboxylation of the perfluorinated nitrogen-containing carboxylates using procedures that are known in the art. Specifically, the fluorinated vinyl amines, 1-propenyl amines, and 2-propenyl amines used in an exemplary preparation of compositions of the general formula I, can be prepared by synthetic procedures known in the art. See for example, U.S. Pat. No. 4,985,556 (Abe et al.).

An illustrative, low cost route for the preparation of the amine-containing fluorinated olefins (including fluorinated vinyl amines, 1-propenylamines and 2-propenylamines) involves the following series of reactions:

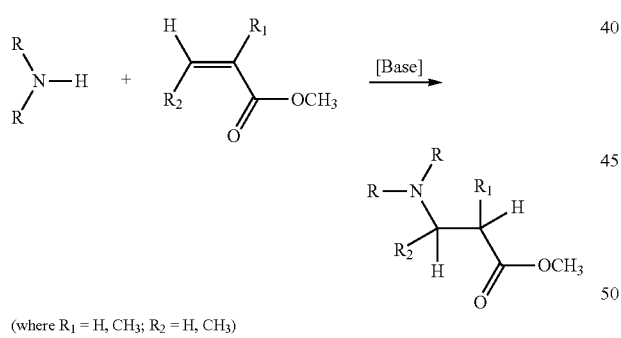

(where $R_1$ = H, $CH_3$; $R_2$ = H, $CH_3$)

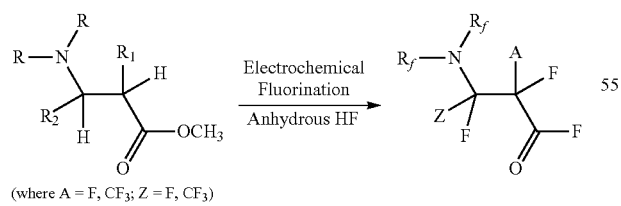

(where A = F, $CF_3$; Z = F, $CF_3$)

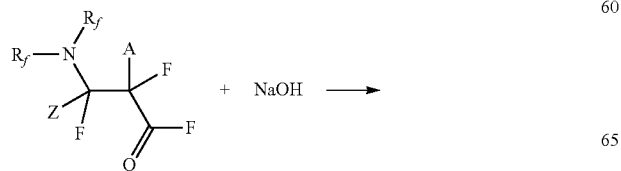

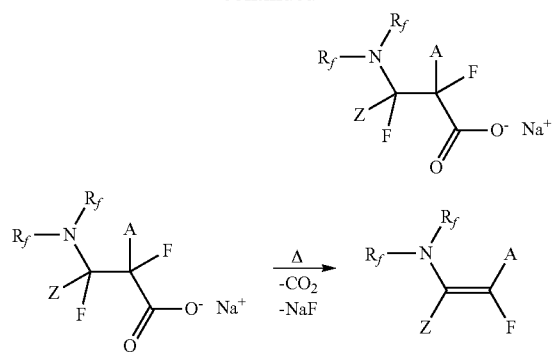

Exemplary perfluorinated vinyl amine and perfluorinated propenyl amines include:

Vinyl amines

1-Propenyl amines
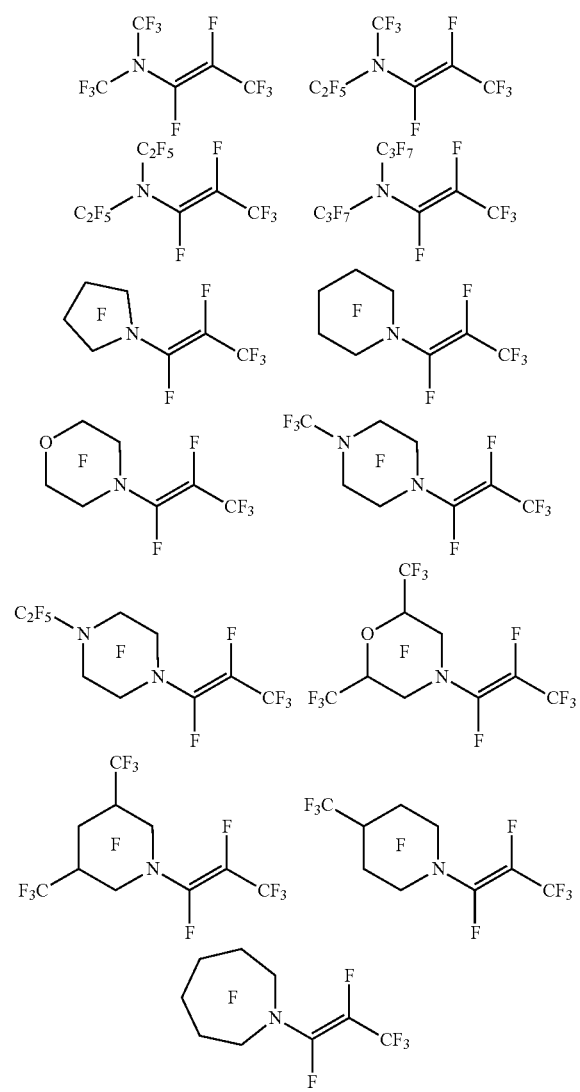
2-Propenyl amines
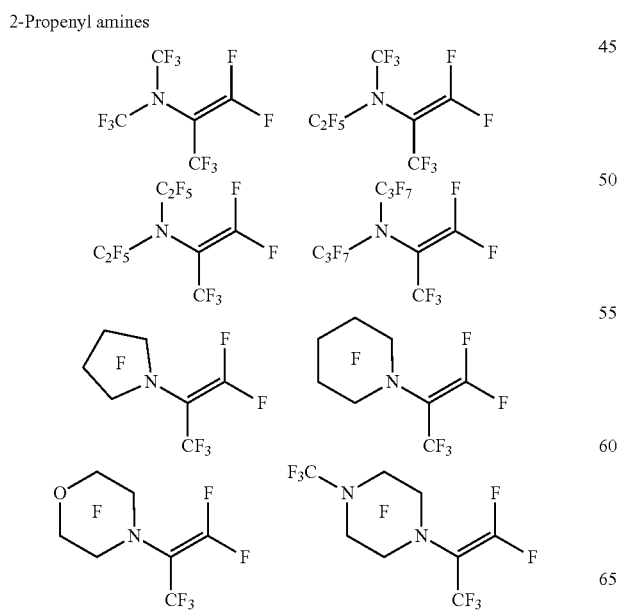
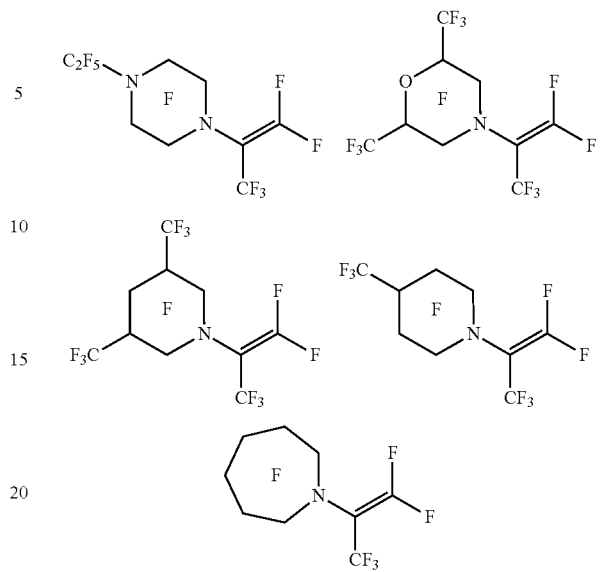
Exemplary fluorinated vinyl amine and fluorinated propenyl amines include:
Vinyl amines
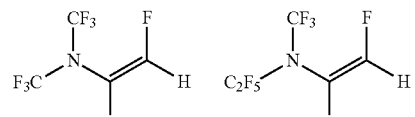
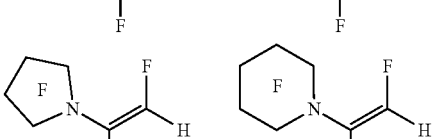
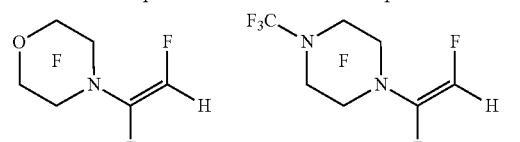
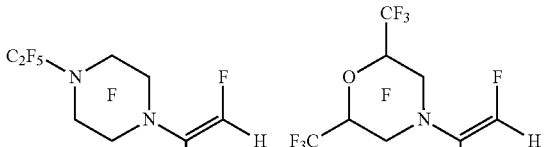

-continued

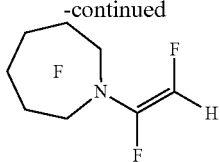

1-Amino propenes

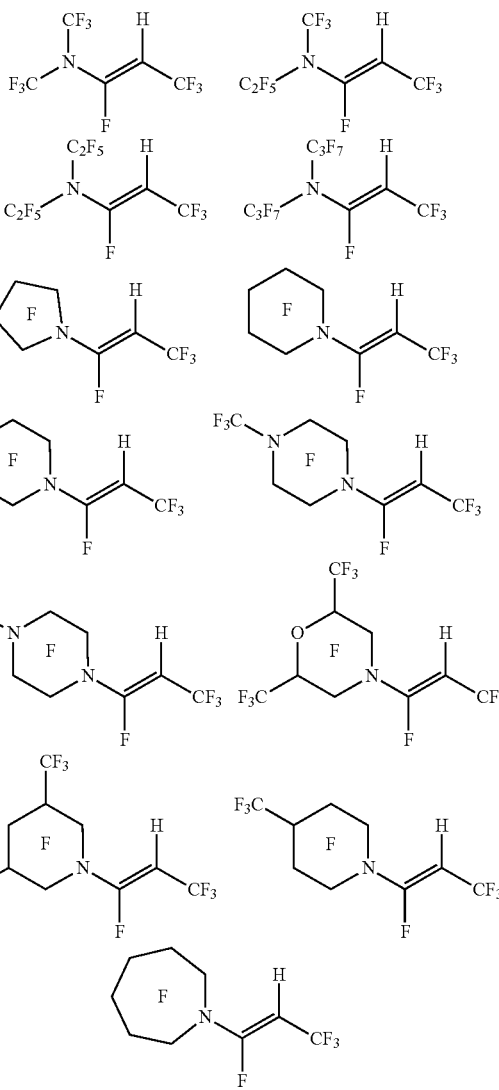

2-Amino propenes

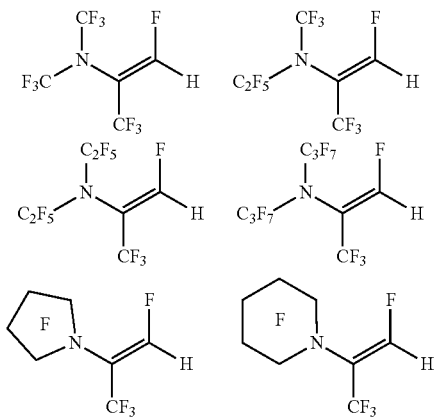

-continued

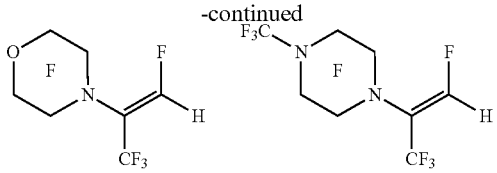

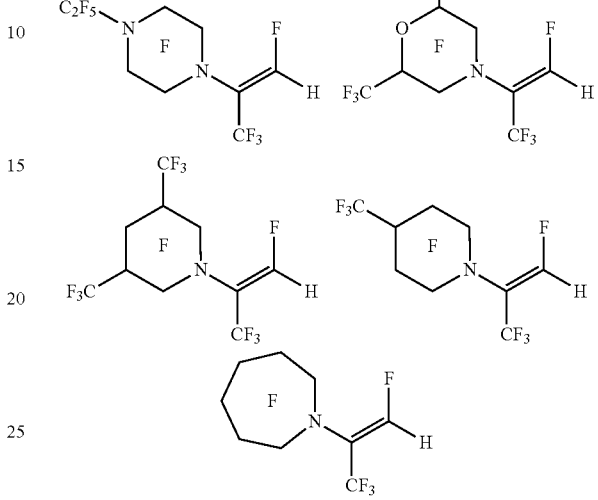

The mole ratio of the amine-containing fluorinated olefin to the acyclic ether may be from 3:1 to 1:6, more preferably 2:1 to 1:3. Depending on the reactivity of the fluorinated olefin and the mole ratio chosen, monosubstituted or disubstituted products can form. For example, a large excess of fluorinated olefin favors the disubstituted product. In other words the amine-containing fluorinated olefin reacts with both carbons adjacent to the ether oxygen atom. In one embodiment, the two fluorinated substituents bonded to the acyclic ether moiety are identical. In other words, —CFZ—CHA-Q is —CFY—CHX—N($R_f^1$)$_2$.

However, in another embodiment, a non-amine-containing fluorinated olefin is reacted with the acyclic ether in addition to the amine-containing fluorinated olefin, to provide one substituent bonded to the acyclic ether ring derived from the amine-containing fluorinated olefin and the another substituent bonded to the acyclic ether ring derived from the non-amine-containing fluorinated olefin. These non-amine-containing fluorinated olefins can provide different chemistry and physical properties to the resulting acyclic fluorinated compound and/or be less costly to manufacture. Such non-amine-containing fluorinated olefins include: pefluorinated olefins, such as tetrafluoroethylene, hexafluoropropylene, chlorotrifluoroethylene, and bromotrifluoroethylene; perfluorinated vinyl ethers, such as perfluoro (methyl vinyl) ether, perfluoro (ethyl vinyl) ether, perfluoro (n-propyl vinyl) ether, perfluoro-2-propoxypropylvinyl ether, perfluoro-3-methoxy-n-propylvinyl ether, perfluoro-2-methoxy-ethylvinyl ether, perfluoro-methoxy-methylvinyl ether ($CF_3$—O—$CF_2$—O—CF=$CF_2$), perfluoro-4,8-dioxa-1-nonene (i.e., $CF_2$=CFO($CF_2$)$_3$O$CF_3$), $C_3F_7$—O—CF($CF_3$)$CF_2$—O—CF=$CF_2$, and $CF_3$—($CF_2$)$_2$—O—CF($CF_3$)—$CF_2$—O—CF($CF_3$)—$CF_2$—O—CF=$CF_2$; perfluorinated allyl ethers, such as perfluoro (methyl allyl) ether ($CF_2$=CF—$CF_2$—O—$CF_3$), perfluoro (ethyl allyl) ether, perfluoro (n-propyl allyl) ether, perfluoro-2-propoxypropyl allyl ether, perfluoro-3-methoxy-n-propylallyl ether, perfluoro-2-methoxy-ethyl allyl ether, perfluoro-methoxymethyl allyl ether, and $CF_3$—$(CF_2)_2$—O—$CF(CF_3)$—$CF_2$—O—$CF(CF_3)$—$CF_2$—O—$CF_2CF$=$CF_2$; $CF_3(CF_2)_n OCF$=CHF where n is an integer of 0-4, $CF_2$=CHF, and $CF_3CF$=CHF. Such non-amine-containing fluorinated olefins are commercially available or can be synthesized using well known methods that have been described in the art.

The non-amine-containing fluorinated olefin and the amine-containing fluorinated olefin may be reacted simultaneously or sequentially with the acyclic ether. Generally, the mole ratio of the non-amine-containing fluorinated olefin to the acyclic ether may be from 3:1 to 1:6, more preferably 2:1 to 1:3. Again, depending on the nature of the non-amine-containing fluorinated olefin and/or its mole ratio, the non-amine-containing fluorinated olefin may add to one or both sides of the acyclic ether. However, in the present disclosure only one non-amine-containing fluorinated olefin is free-radically added to acyclic ether, alpha to the oxygen atom.

The free radical addition of the fluorinated olefin with the acyclic ether is promoted by irradiation or suitable free radical initiating compounds including peroxides, peroxyesters, or peroxycarbonates to generate radicals. Examples of such chemical initiators include tert-amylperoxy-2-ethylhexanoate (available under the trade designation "LUPEROX 575" from Arkema, Crosby, Tex.), lauryl peroxide, tent-butyl peroxide, tert-amylperoxy-2-ethylhexyl carbonate, and mixtures thereof. Irradiation sources include those known in the art, for example, ultraviolet radiation, x-ray radiation, and gamma radiation.

In some embodiments, the fluorinated olefin and the acyclic ether are heated along with a free radical initiator at temperatures of greater than 50, 100, 125, 150, 160 or even 200° C.; and at most 400, 350° C., or even 300° C.

In one embodiment, the resulting fluorinated compounds can be purified to isolate the desired amine-containing acyclic hydrofluoroether. Purification can be done by conventional means including distillation, absorption, extraction, chromatography and recrystallization. The purification can be done to isolate the compound of the present disclosure (in all of its stereoisomeric forms) from impurities, such as starting materials, byproducts, etc. The term "purified form" as used herein means the compound of the present disclosure is at least 90, 95, 98, or even 99 wt. % pure.

The compounds of the present disclosure may be used as a working fluid in a variety of applications. The working fluids may include at least 25%, 50%, 70%, 80%, 90%, 95%, 99%, or even 100% by weight of the above-described formula (I) compounds based on the total weight of the working fluid. In addition to the compounds of the present disclosure, the working fluids may include a total of up to 75%, up to 50%, up to 30%, up to 20%, up to 10%, or up to 5% by weight of one or more of the following components: alcohols, ethers, alkanes, alkenes, haloalkenes, perfluorocarbons, perfluorinated tertiary amines, perfluoroethers, cycloalkanes, esters, ketones, oxiranes, aromatics, siloxanes, unsaturated hydrochlorocarbons, unsaturated hydrochlorofluorocarbons, unsaturated hydrofluorocarbons, non-hetero atom-containing hydrofluoroolefins, hydrochloroolefins, hydrochlorofluoroolefins, unsaturated hydrofluoroethers, or mixtures thereof, based on the total weight of the working fluid. Such additional components can be chosen to modify or enhance the properties of a composition for a particular use.

In one embodiment, the working fluid has no flash point (as measured, for example, following ASTM D-3278-96 e-1).

In one embodiment, the compound of the present disclosure may be used in an apparatus for heat transfer that includes a device and a mechanism for transferring heat to or from the device. The mechanism for transferring heat may include a heat transfer working fluid that includes a compound of formula (I) of the present disclosure.

The provided apparatus for heat transfer may include a device. The device may be a component, work-piece, assembly, etc. to be cooled, heated or maintained at a predetermined temperature or temperature range. Such devices include electrical components, mechanical components and optical components. Examples of devices of the present disclosure include, but are not limited to microprocessors, wafers used to manufacture semiconductor devices, power control semiconductors, electrical distribution switch gear, power transformers, circuit boards, multi-chip modules, packaged and unpackaged semiconductor devices, lasers, chemical reactors, fuel cells, and electrochemical cells. In some embodiments, the device can include a chiller, a heater, or a combination thereof.

In yet other embodiments, the devices can include electronic devices, such as processors, including microprocessors. As these electronic devices become more powerful, the amount of heat generated per unit time increases. Therefore, the mechanism of heat transfer plays an important role in processor performance. The heat-transfer fluid typically has good heat transfer performance, good electrical compatibility (even if used in "indirect contact" applications such as those employing cold plates), as well as low toxicity, low (or non-) flammability and low environmental impact. Good electrical compatibility suggests that the heat-transfer fluid candidate exhibit high dielectric strength, high volume resistivity, and poor solvency for polar materials. Additionally, the heat-transfer fluid should exhibit good mechanical compatibility, that is, it should not affect typical materials of construction in an adverse manner.

The provided apparatus may include a mechanism for transferring heat. The mechanism may include a heat transfer fluid. The heat transfer fluid may include one or more compounds of the present disclosure. Heat may be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism.

The heat transfer mechanism may include facilities for managing the heat-transfer fluid, including, but not limited to pumps, valves, fluid containment systems, pressure control systems, condensers, heat exchangers, heat sources, heat sinks, refrigeration systems, active temperature control systems, and passive temperature control systems. Examples of suitable heat transfer mechanisms include, but are not limited to, temperature controlled wafer chucks in plasma enhanced chemical vapor deposition (PECVD) tools, temperature-controlled test heads for die performance testing, temperature-controlled work zones within semiconductor process equipment, thermal shock test bath liquid reservoirs, and constant temperature baths. In some systems, such as etchers, ashers, PECVD chambers, vapor phase soldering devices, and thermal shock testers, the upper desired operating temperature may be as high as 170° C., as high as 200° C., or even as high as 230° C.

Heat can be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism. The provided apparatus can also include refrigeration systems, cooling systems, testing equipment and machining equipment. In some embodiments, the provided apparatus can be a constant temperature bath or a thermal shock test bath. In some systems, such as etchers, ashers, PECVD chambers, vapor phase soldering devices, and thermal shock testers, the upper desired operating temperature may be as high as 170° C., as high as 200° C., 250 C or even higher.

In some embodiments, the compounds of the present disclosure may be used as a heat transfer agent for use in vapor phase soldering. In using the compounds of the present disclosure in vapor phase soldering, the process described in, for example, U.S. Pat. No. 5,104,034 (Hansen) can be used, which description is hereby incorporated by reference. Briefly, such process includes immersing a component to be soldered in a body of vapor comprising at least an acyclic fluorinated compound of the present disclosure to melt the solder. In carrying out such a process, a liquid pool of the acyclic fluorinated compound (or working fluid that includes the acyclic fluorinated compound) is heated to boiling in a tank to form a saturated vapor in the space between the boiling liquid and a condensing means.

A workpiece to be soldered is immersed in the vapor (at a temperature of greater than 170° C., greater than 200° C., greater than 230° C., 250 C, or even greater), whereby the vapor is condensed on the surface of the workpiece so as to melt and reflow the solder. Finally, the soldered workpiece is then removed from the space containing the vapor.

In another embodiment, the compound of the present disclosure is used in an apparatus for converting thermal energy into mechanical energy in a Rankine cycle. The apparatus may include a working fluid that includes one or more compounds of formula (I). The apparatus may further include a heat source to vaporize the working fluid and form a vaporized working fluid, a turbine through which the vaporized working fluid is passed thereby converting thermal energy into mechanical energy, a condenser to cool the vaporized working fluid after it is passed through the turbine, and a pump to recirculate the working fluid.

In some embodiments, the present disclosure relates to a process for converting thermal energy into mechanical energy in a Rankine cycle. The process may include using a heat source to vaporize a working fluid that includes one or more compounds of formula (I) to form a vaporized working fluid. In some embodiments, the heat is transferred from the heat source to the working fluid in an evaporator or boiler. The vaporized working fluid may pressurized and can be used to do work by expansion. The heat source can be of any form such as from fossil fuels, e.g., oil, coal, or natural gas. Additionally, in some embodiments, the heat source can come from nuclear power, solar power, or fuel cells. In other embodiments, the heat can be "waste heat" from other heat transfer systems that would otherwise be lost to the atmosphere. The "waste heat," in some embodiments, can be heat that is recovered from a second Rankine cycle system from the condenser or other cooling device in the second Rankine cycle.

An additional source of "waste heat" can be found at landfills where methane gas is flared off. In order to prevent methane gas from entering the environment and thus contributing to global warming, the methane gas generated by the landfills can be burned by way of "flares" producing carbon dioxide and water which are both less harmful to the environment in terms of global warming potential than methane. Other sources of "waste heat" that can be useful in the provided processes are geothermal sources and heat from other types of engines such as gas turbine engines that give off significant heat in their exhaust gases and to cooling liquids such as water and lubricants.

In the provided process, the vaporized working fluid may expanded though a device that can convert the pressurized working fluid into mechanical energy. In some embodiments, the vaporized working fluid is expanded through a turbine which can cause a shaft to rotate from the pressure of the vaporized working fluid expanding. The turbine can then be used to do mechanical work such as, in some embodiments, operate a generator, thus generating electricity. In other embodiments, the turbine can be used to drive belts, wheels, gears, or other devices that can transfer mechanical work or energy for use in attached or linked devices.

After the vaporized working fluid has been converted to mechanical energy the vaporized (and now expanded) working fluid can be condensed using a cooling source to liquefy for reuse. The heat released by the condenser can be used for other purposes including being recycled into the same or another Rankine cycle system, thus saving energy. Finally, the condensed working fluid can be pumped by way of a pump back into the boiler or evaporator for reuse in a closed system.

The desired thermodynamic characteristics of organic Rankine cycle working fluids are well known to those of ordinary skill and are discussed, for example, in U.S. Pat. Appl. Publ. No. 2010/0139274 (Zyhowski et al.). The greater the difference between the temperature of the heat source and the temperature of the condensed liquid or a provided heat sink after condensation, the higher the Rankine cycle thermodynamic efficiency. The thermodynamic efficiency is influenced by matching the working fluid to the heat source temperature. The closer the evaporating temperature of the working fluid to the source temperature, the higher the efficiency of the system. Toluene can be used, for example, in the temperature range of 79° C. to about 260° C., however toluene has toxicological and flammability concerns. Fluids such as 1,1-dichloro-2,2,2-trifluoroethane and 1,1,1,3,3-pentafluoropropane can be used in this temperature range as an alternative. But 1,1-dichloro-2,2,2-trifluoroethane can form toxic compounds below 300° C. and need to be limited to an evaporating temperature of about 93° C. to about 121° C. Thus, there is a desire for other environmentally-friendly Rankine cycle working fluids with higher critical temperatures so that source temperatures such as gas turbine and internal combustion engine exhaust can be better matched to the working fluid.

In one embodiment, the compound of the present disclosure is used in a cleaning compositions along with one or more co-solvents. In some embodiments, the present disclosure relates to a process for cleaning a substrate. The cleaning process can be carried out by contacting a contaminated substrate with a cleaning composition. The compound of the present disclosure can be utilized alone or in admixture with each other or with other commonly-used cleaning co-solvents. Representative examples of co-solvents which can be used in the cleaning composition include methanol, ethanol, isopropanol, t-butyl alcohol, methyl t-butyl ether, methyl t-amyl ether, 1,2-dimethoxyethane, cyclohexane, 2,2,4-trimethylpentane, n-decane, terpenes (e.g., a-pinene, camphene, and limonene), trans-1,2-dichloroethylene, cis-1,2-dichloroethylene, methylcyclopentane, decalin, methyl decanoate, t-butyl acetate, ethyl acetate, diethyl phthalate, 2-butanone, methyl isobutyl ketone, naphthalene, toluene, p-chlorobenzotrifluoride, trifluorotoluene, bis(trifluoromethyl)benzenes, hexamethyl disiloxane, octamethyl trisiloxane, perfluorohexane, perfluoroheptane, perfluorooctane, perfluorotributylamine, perfluoro-N-methyl morpholine, perfluoro-2-butyl oxacyclopentane, methylene chloride, chlorocyclohexane, 1-chlorobutane, 1,1-dichloro-1-fluoroethane, 1,1,1-trifluoro-2,2-dichloroethane, 1,1,1,2,2-pentafluoro-3,3-dichloropropane, 1,1,2,2,3-pentafluoro-1,3-dichloropropane, 2,3-dihydroperfluoropentane, 1,1,1,2,2,4-hexafluorobutane, 1-trifluoromethyl-1,2,2-trifluorocyclobutane, 3-methyl-1,1,2,2-tetrafluorocyclobutane, 1-hydropentadecafluoroheptane, or mixtures thereof. Such co-solvents can be chosen to modify or enhance the solvency properties of a cleaning composition for a particular use and can be utilized in ratios (of co-solvent to compounds according to formula (I)) such that the resulting composition has no flash point. If desirable for a particular application, the cleaning composition can further contain one or more dissolved or dispersed gaseous, liquid, or solid additives (for example, carbon dioxide gas, surfactants, stabilizers, antioxidants, or activated carbon).

In some embodiments, the present disclosure relates to cleaning compositions that include one or more compounds of the present disclosure and optionally one or more surfactants. Suitable surfactants include those surfactants that are sufficiently soluble in the compound of the present disclosure, and which promote soil removal by dissolving, dispersing or displacing the soil. One useful class of surfactants are those nonionic surfactants that have a hydrophilic-lipophilic balance (HLB) value of less than about 14. Examples include ethoxylated alcohols, ethoxylated alkylphenols, ethoxylated fatty acids, alkylaryl sulfonates, glycerol esters, ethoxylated fluoroalcohols, and fluorinated sulfonamides. Mixtures of surfactants having complementary properties may be used in which one surfactant is added to the cleaning composition to promote oily soil removal and another added to promote water-soluble soil removal. The surfactant, if used, can be added in an amount sufficient to promote soil removal. Typically, surfactant may be added in amounts from 0.1 to 5.0 wt. % or from 0.2 to 2.0 wt. % of the cleaning composition.

The cleaning compositions can be used in either the gaseous or the liquid state (or both), and any of known or future techniques for "contacting" a substrate can be utilized. For example, a liquid cleaning composition can be sprayed or brushed onto the substrate, a gaseous cleaning composition can be blown across the substrate, or the substrate can be immersed in either a gaseous or a liquid composition. Elevated temperatures, ultrasonic energy, and/or agitation can be used to facilitate the cleaning. Various different solvent cleaning techniques are described by B. N. Ellis in *Cleaning and Contamination of Electronics Components and Assemblies,* Electrochemical Publications Limited, Ayr, Scotland, pages 182-94 (1986).

Both organic and inorganic substrates can be cleaned by the processes of the present disclosure. Representative examples of the substrates include metals; ceramics; glass; polycarbonate; polystyrene; acrylonitrile-butadiene-styrene copolymer; natural fibers (and fabrics derived therefrom) such as cotton, silk, fur, suede, leather, linen, and wool; synthetic fibers (and fabrics) such as polyester, rayon, acrylics, nylon, or blends thereof; fabrics comprising a blend of natural and synthetic fibers; and composites of the foregoing materials. In some embodiments, the process may be used in the precision cleaning of electronic components (e.g., circuit boards), optical or magnetic media, or medical devices.

In still another embodiment, the compound of the present disclosure is used in a dielectric fluids, which can be used in electrical devices (e.g., capacitors, switchgear, transformers, or electric cables or buses). For purposes of the present application, the term "dielectric fluid" is inclusive of both liquid dielectrics and gaseous dielectrics. The physical state of the fluid, gaseous or liquid, is determined at the operating conditions of temperature and pressure of the electrical device in which it is used.

In some embodiments, the dielectric fluids include one or more compounds of formula (I) and, optionally, one or more second dielectric fluids. Suitable second dielectric fluids include, for example, air, nitrogen, helium, argon, and carbon dioxide, or combinations thereof. The second dielectric fluid may be a non-condensable gas or an inert gas. Generally, the second dielectric fluid may be used in amounts such that vapor pressure is at least 70 kPa at 25° C., or at the operating temperature of the electrical device.

The dielectric fluids of the present application comprising the compounds of formula (I) are useful for electrical insulation and for arc quenching and current interruption equipment used in the transmission and distribution of electrical energy. Generally, there are three major types of electrical devices in which the fluids of the present disclosure can be used: (1) gas-insulated circuit breakers and current-interruption equipment, (2) gas-insulated transmission lines, and (3) gas-insulated transformers. Such gas-insulated equipment is a major component of power transmission and distribution systems.

In some embodiments, the present disclosure provides electrical devices, such as capacitors, comprising metal electrodes spaced from each other such that the gaseous dielectric fills the space between the electrodes. The interior space of the electrical device may also comprise a reservoir of the liquid dielectric fluid which is in equilibrium with the gaseous dielectric fluid. Thus, the reservoir may replenish any losses of the dielectric fluid.

In another embodiment, the present disclosure relates to coating compositions comprising (a) a solvent composition that includes one or more compounds of the present disclosure, and (b) one or more coating materials which are soluble or dispersible in the solvent composition.

In various embodiments, the coating materials of the coating compositions may include pigments, lubricants, stabilizers, adhesives, anti-oxidants, dyes, polymers, pharmaceuticals, release agents, inorganic oxides, and the like, and combinations thereof. For example, coating materials may include unsaturated perfluoropolyether, unsaturated hydrocarbon, and silicone lubricants; amorphous copolymers of tetrafluoroethylene; polytetrafluoroethylene; or combinations thereof. Further examples of suitable coating materials include titanium dioxide, iron oxides, magnesium oxide, unsaturated perfluoropolyethers, polysiloxanes, stearic acid, acrylic adhesives, polytetrafluoroethylene, amorphous copolymers of tetrafluoroethylene, or combinations thereof.

In some embodiments, the above-described coating compositions can be useful in coating deposition, where the compounds of Formula (I) function as a carrier for a coating material to enable deposition of the material on the surface of a substrate. In this regard, the present disclosure further relates to a process for depositing a coating on a substrate surface using the coating composition. The process comprises the step of applying to at least a portion of at least one surface of a substrate a coating of a liquid coating composition comprising (a) a solvent composition containing one or more of the compounds of formula (I); and (b) one or more coating materials which are soluble or dispersible in the solvent composition. The solvent composition can further comprise one or more co-dispersants or co-solvents and/or one or more additives (e.g., surfactants, coloring agents, stabilizers, anti-oxidants, flame retardants, and the like). Preferably, the process further comprises the step of removing the solvent composition from the coating by, e.g., allowing evaporation (which can be aided by the application of, e.g., heat or vacuum).

In various embodiments, to form a coating composition, the components of the coating composition (i.e., the compound(s) of formula (I), the coating material(s), and any co-dispersant(s) or co-solvent(s) utilized) can be combined by any conventional mixing technique used for dissolving, dispersing, or emulsifying coating materials, e.g., by mechanical agitation, ultrasonic agitation, manual agitation, and the like. The solvent composition and the coating material(s) can be combined in any ratio depending upon the desired thickness of the coating. For example, the coating material(s) may constitute from about 0.1 to about 10 weight percent of the coating composition.

In illustrative embodiments, the deposition process of the disclosure can be carried out by applying the coating composition to a substrate by any conventional technique. For example, the composition can be brushed or sprayed (e.g., as an aerosol) onto the substrate, or the substrate can be spin-coated. In some embodiments, the substrate may be coated by immersion in the composition. Immersion can be carried out at any suitable temperature and can be maintained for any convenient length of time. If the substrate is a tubing, such as a catheter, and it is desired to ensure that the composition coats the lumen wall, the composition may be drawn into the lumen by the application of reduced pressure.

In various embodiments, after a coating is applied to a substrate, the solvent composition can be removed from the coating (e.g., by evaporation). If desired, the rate of evaporation can be accelerated by application of reduced pressure or mild heat. The coating can be of any convenient thickness, and, in practice, the thickness will be determined by such factors as the viscosity of the coating material, the temperature at which the coating is applied, and the rate of withdrawal (if immersion is utilized).

Both organic and inorganic substrates can be coated by the processes of the present disclosure. Representative examples of the substrates include metals, ceramics, glass, polycarbonate, polystyrene, acrylonitrile-butadiene-styrene copolymer, natural fibers (and fabrics derived therefrom) such as cotton, silk, fur, suede, leather, linen, and wool, synthetic fibers (and fabrics) such as polyester, rayon, acrylics, nylon, or blends thereof, fabrics including a blend of natural and synthetic fibers, and composites of the foregoing materials. In some embodiments, substrates that may be coated include, for example, magnetic hard disks or electrical connectors with perfluoropolyether lubricants or medical devices with silicone lubricants.

In some embodiments, the present disclosure further relates to electrolyte compositions that include one or more compounds of the present disclosure. The electrolyte compositions may comprise (a) a solvent composition including one or more of the compounds according to formula (I); and (b) at least one electrolyte salt. The electrolyte compositions of the present disclosure exhibit excellent oxidative stability, and when used in high voltage electrochemical cells (such as rechargeable lithium ion batteries) provide outstanding cycle life and calendar life. For example, when such electrolyte compositions are used in an electrochemical cell with a graphitized carbon electrode, the electrolytes provide stable cycling to a maximum charge voltage of at least 4.5V and up to 6.0V vs. $Li/Li^+$.

Electrolyte salts that are suitable for use in preparing the electrolyte compositions of the present disclosure include those salts that comprise at least one cation and at least one weakly coordinating anion (the conjugate acid of the anion having an acidity greater than or equal to that of a hydrocarbon sulfonic acid (for example, $PF_6^-$ anion or a bis(perfluoroalkanesulfonyl)imide anion); that are at least partially soluble in a selected compound of formula (I) (or in a blend thereof with one or more other compounds of formula (I) or one or more conventional electrolyte solvents); and that at least partially dissociate to form a conductive electrolyte composition. The salts may be stable over a range of operating voltages, are non-corrosive, and may be thermally and hydrolytically stable. Suitable cations include alkali metal, alkaline earth metal, Group IIB metal, Group IIIB metal, transition metal, rare earth metal, and ammonium (for example, tetraalkylammonium or trialkylammonium) cations, as well as a proton. In some embodiments, cations for battery use include alkali metal and alkaline earth metal cations. Suitable anions include fluorine-containing inorganic anions such as $(FSO_2)_2N^-$, $BF_4^-$, $PF_6^-$, $AsF_6^-$, and $SbF_6^-$; $ClO_4^-$; $HSO_4^-$; $H_2PO_4^-$; organic anions such as alkane, aryl, and alkaryl sulfonates; fluorine-containing and nonfluorinated tetraarylborates; carboranes and halogen-, alkyl-, or haloalkylsubstituted carborane anions including metallocarborane anions; and fluorine-containing organic anions such as perfluoroalkanesulfonates, cyanoperfluoroalkanesulfonylamides, bis(cyano)perfluoroalkanesulfonylmethides, (perfluoroalkanesulfonyl)imides, bis(perfluoroalkanesulfonyl)methides, and tris(perfluoroalkanesulfonyl)methides; and the like. Preferred anions for battery use include fluorine-containing inorganic anions (for example, $(FSO_2)_2N^-$, $BF_4^-$, $PF_6^-$, and $AsF_6^-$) and fluorine-containing organic anions (for example, perfluoroalkanesulfonates, bis(perfluoroalkanesulfonyl)imides, and tris(perfluoroalkanesulfonyl)methides). The fluorine-containing organic anions can be either fully fluorinated, that is perfluorinated, or partially fluorinated (within the organic portion thereof). In some embodiments, the fluorine-containing organic anion is at least about 80 percent fluorinated (that is, at least about 80 percent of the carbon-bonded substituents of the anion are fluorine atoms). In some embodiments, the anion is perfluorinated. The anions, including the perfluorinated anions, can contain one or more catenary heteroatoms such as, for example, nitrogen, oxygen, or sulfur. In some embodiments, fluorine-containing organic anions include perfluoroalkanesulfonates, bis(perfluoroalkanesulfonyl)imides, and tris(perfluoroalkanesulfonyl)methides.

In some embodiments, the electrolyte salts may include lithium salts. Suitable lithium salts include, for example, lithium hexafluorophosphate, lithium bis(trifluoromethanesulfonyl)imide, lithium bis(perfluoroethanesulfonyl)imide, lithium tetrafluoroborate, lithium perchlorate, lithium hexafluoroarsenate, lithium trifluoromethanesulfonate, lithium tris(trifluoromethanesulfonyl)methide, lithium bis(fluorosulfonyl)imide (Li—FSI), and mixtures of two or more thereof.

The electrolyte compositions of the present disclosure can be prepared by combining at least one electrolyte salt and a solvent composition including at least one compound of formula (I), such that the salt is at least partially dissolved in the solvent composition at the desired operating temperature. The compounds of the present disclosure (or a normally liquid composition including, consisting, or consisting essentially thereof) can be used in such preparation.

In some embodiments, the electrolyte salt is employed in the electrolyte composition at a concentration such that the conductivity of the electrolyte composition is at or near its maximum value (typically, for example, at a Li molar concentration of around 0.1-4.0 M, or 1.0-2.0 M, for electrolytes for lithium batteries), although a wide range of other concentrations may also be employed.

In some embodiments, one or more conventional electrolyte solvents are mixed with the compound(s) of formula (I) (for example, such that the compound(s) of formula (I) constitute from about 1 to about 80 or 90 percent of the resulting solvent composition). Useful conventional electrolyte solvents include, for example, organic and fluorine-containing electrolyte solvents (for example, propylene carbonate, ethylene carbonate, dimethyl carbonate, diethyl carbonate, ethyl methyl carbonate, dimethoxyethane, 7-butyrolactone, diglyme (that is, diethylene glycol dimethyl ether), tetraglyme (that is, tetraethylene glycol dimethyl ether), monofluoroethylene carbonate, vinylene carbonate, ethyl acetate, methyl butyrate, tetrahydrofuran, alkyl-substituted tetrahydrofuran, 1,3-dioxolane, alkyl-substituted 1,3-dioxolane, tetrahydropyran, alkyl-substituted tetrahydropyran, and the like, and mixtures thereof). Other conventional electrolyte additives (for example, a surfactant) can also be present, if desired.

The present disclosure further relates to electrochemical cells (e.g., fuel cells, batteries, capacitors, electrochromic windows) that include the above-described electrolyte compositions. Such an electrochemical cell may include a positive electrode, a negative electrode, a separator, and the above-described electrolyte composition.

A variety of negative and positive electrodes may be employed in the electrochemical cells. Representative negative electrodes include graphitic carbons e.g., those having a spacing between (002) crystallographic planes, $d_{002}$, of 3.45 Å>$d_{002}$>3.354 Å and existing in forms such as powders, flakes, fibers or spheres (e.g., mesocarbon microbeads); $Li_{4/3}Ti_{5/3}O_4$ the lithium alloy compositions described in U.S. Pat. No. 6,203,944 (Turner et al.) and U.S. Pat. No. 6,255,017 (Turner); and combinations thereof. Representative positive electrodes include $LiFePO_4$, $LiMnPO_4$, $LiCoPO_4$, $LiMn_2O_4$, $LiCoO_2$ and combinations thereof. The negative or positive electrode may contain additives such as will be familiar to those skilled in the art, e.g., carbon black for negative electrodes and carbon black, flake graphite and the like for positive electrodes.

The electrochemical devices of the present disclosure can be used in various electronic articles such as computers, power tools, automobiles, telecommunication devices, and the like.

Exemplary embodiments of the present disclosure include, but should not be limited to, the following:

Embodiment 1. A acyclic fluorinated compound of formula (I)

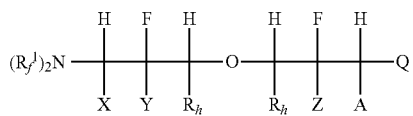

where:

each $R_h$ is independently H or $CH_3$;

X is selected from F or $CF_3$, and Y is selected from H, F, or $CF_3$, wherein when X is $CF_3$ then Y is F and when Y is $CF_3$ then X is F;

each $R_f^1$ is independently selected from a linear or branched perfluorinated alkyl group comprising 1-8 carbon atoms and optionally comprising at least one catenated atom selected from O, N, or combinations thereof; or the two $R_f^1$ groups are bonded together to form a fluorinated ring structure comprising 4-8 carbon atoms and optionally comprising at least one catenated atom selected from O, N, or combinations thereof;

A is selected from F, or $CF_3$;

Z is selected from H, F or $CF_3$; and

Q is selected from (i) a F atom, (ii) a Cl atom, (iii) a linear, cyclic, or branched perfluorinated alkyl group comprising 1-8 carbon atoms and optionally comprising at least one catenated atom selected from O, N, or combinations thereof, or (iv) a $G(R_f^2)_e$ group, where G is an O atom or a N atom wherein:

when Q is a Cl atom, then Z and A are F atoms;

when G is O then e is 1, Z is H, F or $CF_3$; A is F; and $R_f^2$ is a linear or branched perfluorinated alkyl group comprising 1-10 carbon atoms and optionally comprising at least one catenated atom selected from O, N, or combinations thereof;

when G is N then e is 2, and each $R_f^2$ group is independently a linear or branched perfluorinated alkyl group comprising 1-8 carbon atoms and optionally comprising at least one catenated atom selected from O, N, or combinations thereof or the two $R_f^2$ groups are bonded together to form a fluorinated ring structure comprising 4-8 carbon atoms and optionally comprising at least one catenated atom selected from O, N, or combinations thereof, with the proviso that when A is $CF_3$ then Z is F, and when Z is $CF_3$ then A is F.

Embodiment 2. The acyclic fluorinated compound of embodiment 1, wherein $Q=N(R_f^1)_2$.

Embodiment 3. The acyclic fluorinated compound of any one of the previous embodiments, wherein $N(R_f^1)_2$ is a perfluorinated morpholine group.

Embodiment 4. The acyclic fluorinated compound of embodiment 1, wherein Q is a perfluorinated alkyl group comprising less than 4 carbon atoms.

Embodiment 5. The acyclic fluorinated compound of any one of the previous embodiments, wherein X and Y are both F.

Embodiment 6. The acyclic fluorinated compound of any one of the previous embodiments, wherein A and Z are both F.

Embodiment 7. The acyclic fluorinated compound of any one of the previous embodiments, wherein the unsaturated fluorinated compound comprises at least one of the following:

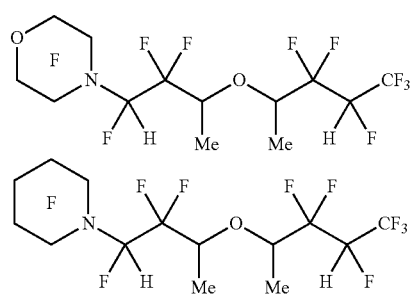

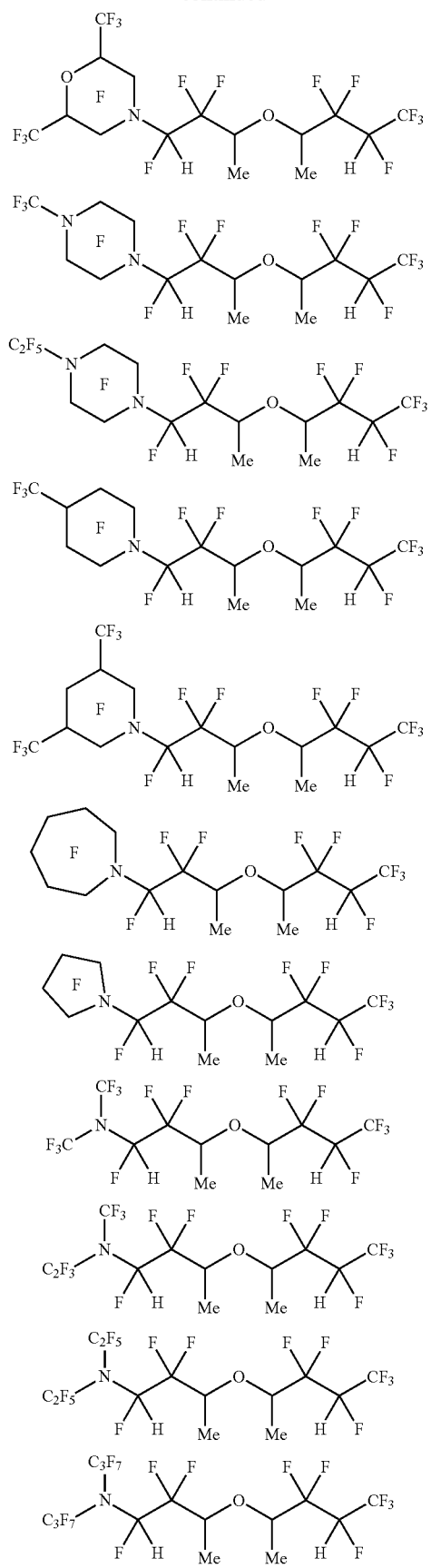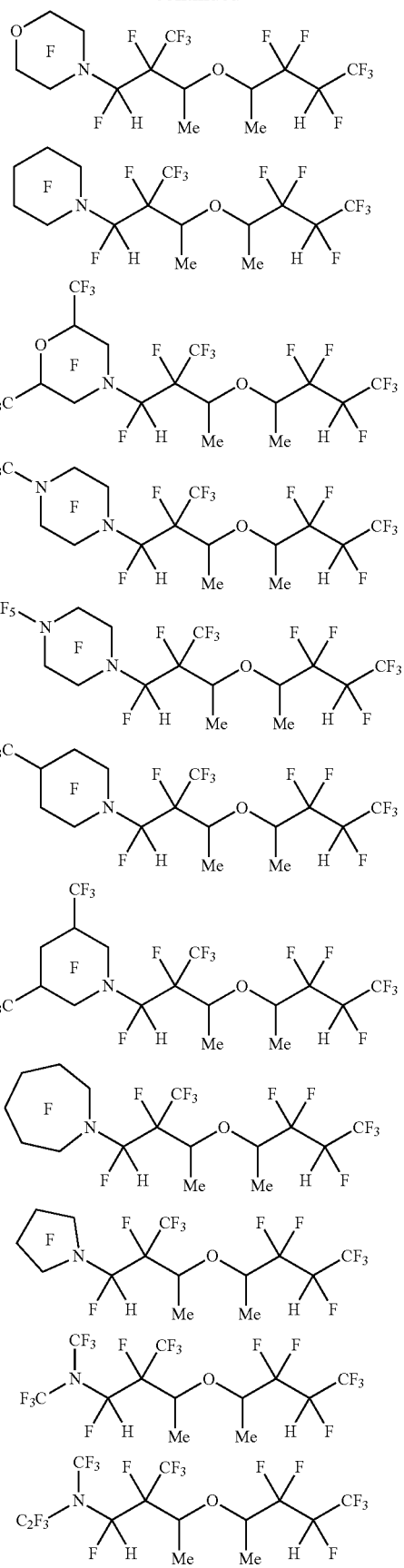

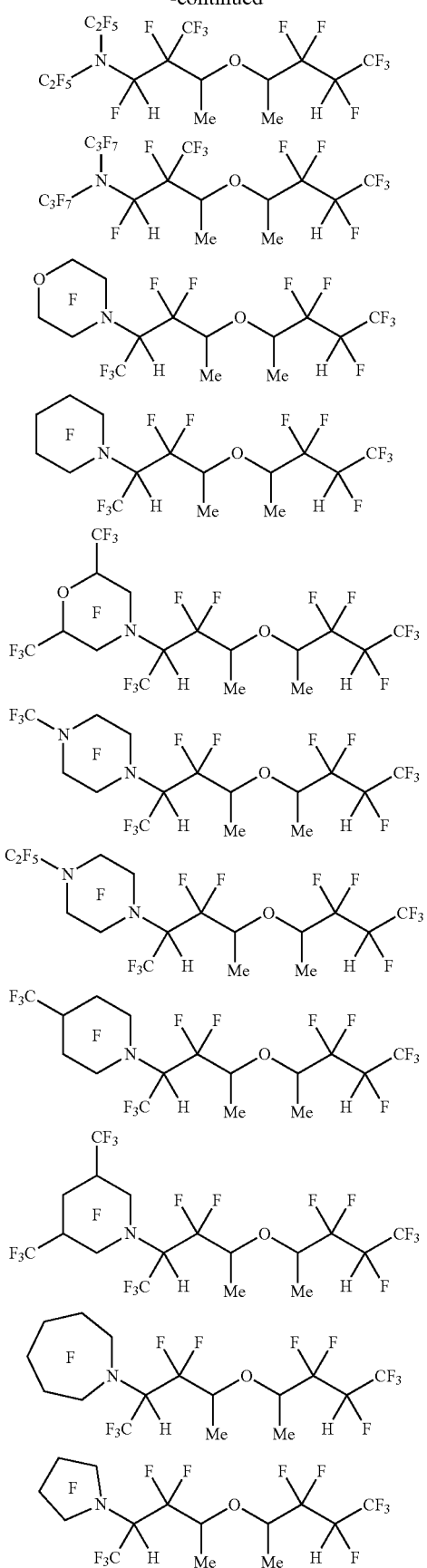
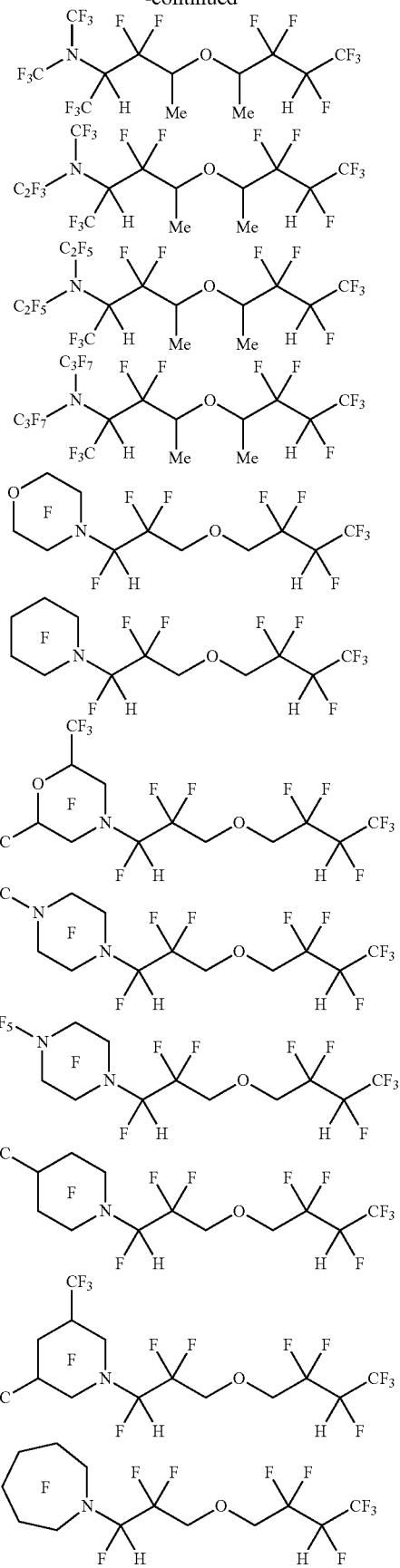

-continued
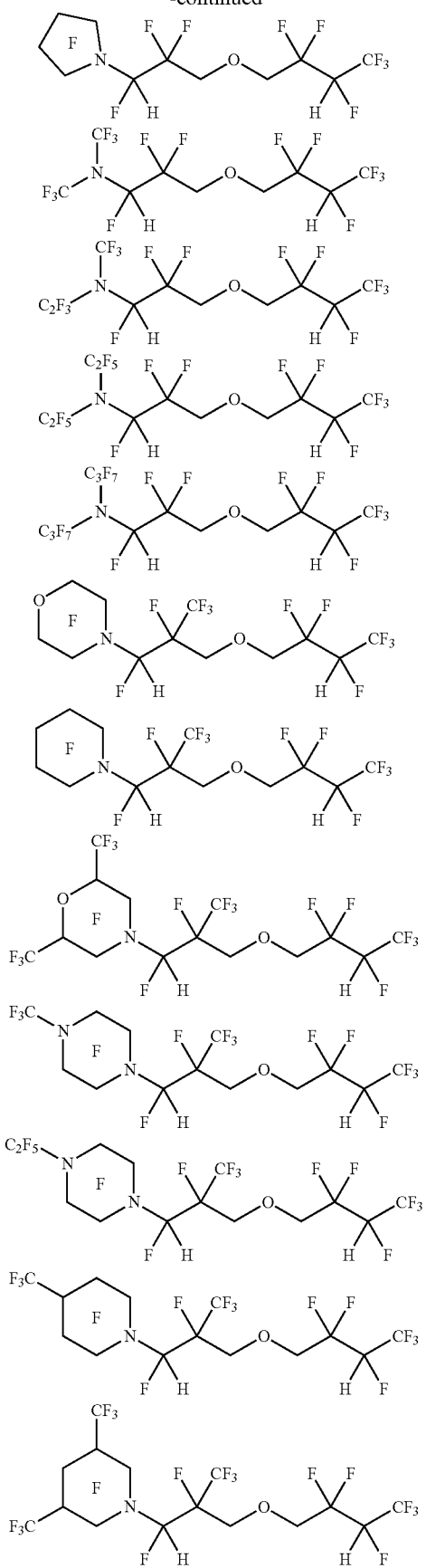
-continued
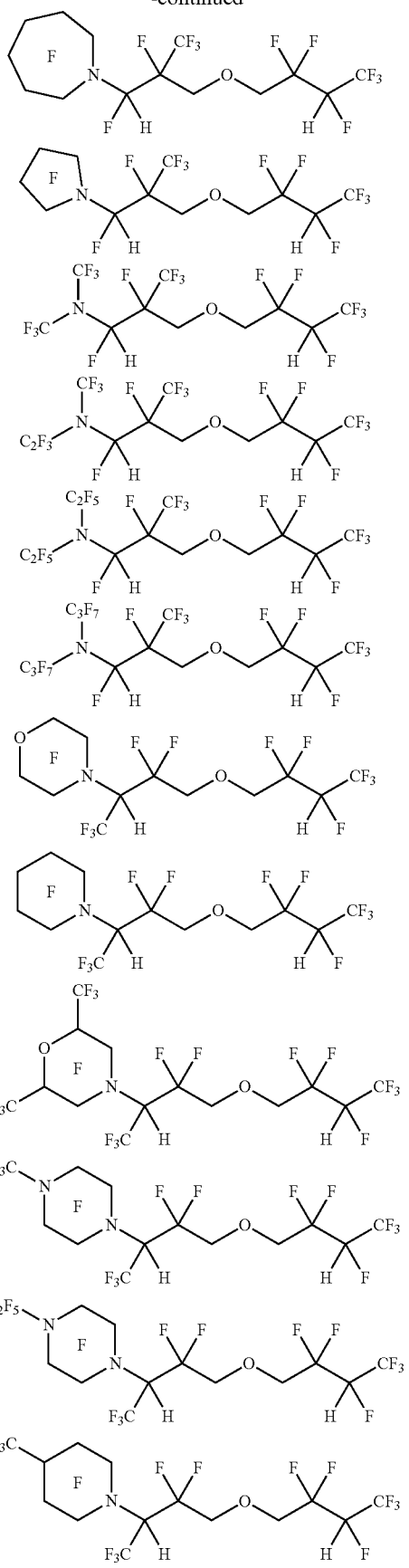

-continued

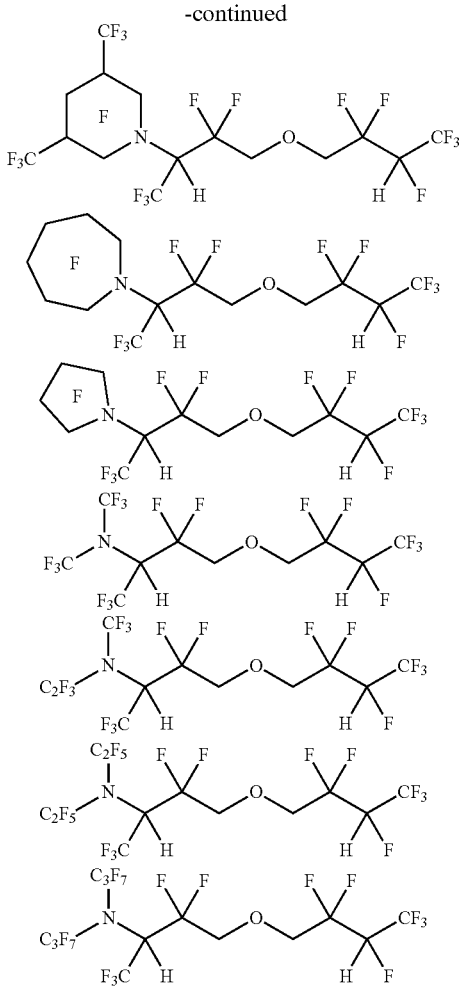

where Me refers to a methyl group.

Embodiment 8. The acyclic fluorinated compound of any one of the previous embodiments, wherein the acyclic fluorinated compound is nonflammable based on closed-cup flashpoint testing following ASTM D-327-96 e-1.

Embodiment 9. The acyclic fluorinated compound of any one of the previous embodiments, wherein the acyclic fluorinated compound has a global warming potential of less than 100.

Embodiment 10. The acyclic fluorinated compound of any one of the previous embodiments, wherein the acyclic fluorinated compound is nonflammable based on closed-cup flashpoint testing following ASTM D-327-96 e-1.

Embodiment 11. The acyclic fluorinated compound of any one of the previous embodiments, wherein the acyclic fluorinated compound has a global warming potential of less than 100.

Embodiment 12. A working fluid comprising the acyclic fluorinated compound according to any one of the previous embodiments, wherein the acyclic fluorinated compound is present in the working fluid in an amount of at least 25% by weight based on the total weight of the working fluid.

Embodiment 13. The working fluid of embodiment 12, wherein the working fluid further comprises a co-solvent.

Embodiment 14. Use of the acyclic fluorinated compound of any one embodiments 1-11, wherein the acyclic fluorinated compound is in a cleaning composition.

Embodiment 15. Use of the acyclic fluorinated compound of any one embodiments 1-11, wherein the acyclic fluorinated compound is an electrolyte solvent or additive.

Embodiment 16. Use of the acyclic fluorinated compound of any one embodiments 1-11, wherein the acyclic fluorinated compound is a heat transfer fluid.

Embodiment 17. Use of the acyclic fluorinated compound of any one embodiments 1-11, wherein the acyclic fluorinated compound is a vapor phase soldering fluid.

Embodiment 18. An apparatus for heat transfer comprising:
a device; and
a mechanism for transferring heat to or from the device, the mechanism comprising a heat transfer fluid that comprises the acyclic fluorinated compound according to any one of embodiments 1-11.

Embodiment 19. An apparatus for heat transfer according to embodiment 18, wherein the device is selected from a microprocessor, a semiconductor wafer used to manufacture a semiconductor device, a power control semiconductor, an electrochemical cell, an electrical distribution switch gear, a power transformer, a circuit board, a multi-chip module, a packaged or unpackaged semiconductor device, a fuel cell, and a laser.

Embodiment 20. An apparatus according to any one of embodiments 18-19, wherein the mechanism for transferring heat is a component in a system for maintaining a temperature or temperature range of an electronic device.

Embodiment 21. An apparatus according to any one of embodiments 18-20, wherein the device comprises an electronic component to be soldered.

Embodiment 22. An apparatus according to any one of embodiments 18-21, wherein the mechanism comprises vapor phase soldering.

Embodiment 23. A method of transferring heat comprising:
providing a device; and
transferring heat to or from the device using a heat transfer fluid that comprises a acyclic fluorinated compound according to any one of embodiments 1-11.

Embodiment 24. A composition comprising a purified form of the acyclic fluorinated compound according to any one of embodiments 1-11.

EXAMPLES

Unless otherwise noted, all parts, percentages, ratios, etc. in the examples and the rest of the specification are by weight, and all reagents used in the examples were obtained, or are available, from general chemical suppliers such as, for example, Sigma-Aldrich Corp., Saint Louis, Mo., or may be synthesized by conventional methods.

The following abbreviations are used in this section: mL=milliliter, min=minutes, h=hours, g=gram, mol=mole, mmol=millimole.

The following abbreviations are used in this section: mL=milliliter, min=minutes, h=hours, g=gram, kPa=kilopascal, psi=pounds per square inch, mol=mole, mmol=millimole, GC=gas chromatography, GC-MS=gas chromatography-mass spectrometry.

TABLE 1

Materials List

| Material | Description |
|---|---|
| Diethyl ether | Commercially available from Sigma-Aldrich Corp. |
| Dimethyl ether | Commercially available from Sigma-Aldrich Corp. |
| tert-Butanol | Commercially available from Sigma-Aldrich Corp. |
| TAPEH | tert-Amylperoxy-2-ethylhexanoate, available as LUPEROX 575 from Arkema, Crosby, TX. |
| HFP | Hexafluoropropene, commercially available from Sigma-Aldrich Corp. |
| tBuOOtBu | tert-Butyl peroxide, commercially available from Sigma-Aldrich Corp. |
| MVA | 2,2,3,3,5,5,6,6-octafluoro-4-(1,2,2-trifluorovinyl)morpholine, which may be synthesized by the methods described in Abe et al. *Chem. Lett.* 1988, 1887-1890; Abe et al. *Chem. Lett.* 1989, 905-908. |
| Pf vinyl pyrrolidine | 2,2,3,3,4,4,5,5-octafluoro-1-(1,2,2-trifluorovinyl)pyrrolidine, which may be synthesized by the methods described in Abe et al. *Chem. Lett.* 1988, 1887-1890; Abe et al. *Chem. Lett.* 1989, 905-908. |
| Pf N-Et-N-(1-propenyl)piperazine | 2,2,3,3,5,5,6,6-octafluoro-1-(perfluoroethyl)-4-(perfluoroprop-1-en-1-yl)piperazine, which may be synthesized by the methods described in Abe et al. *Chem. Lett.* 1988, 1887-1890; Abe et al. *Chem. Lett.* 1989, 905-908. |
| M-1P | 2,2,3,3,5,5,6,6-octafluoro-4-(perfluoroprop-1-en-1-yl)morpholine, which may be synthesized by the methods described in Abe et al. *Chem. Lett.* 1988, 1887-1890; Abe et al. *Chem. Lett.* 1989, 905-908. |

Example 1(EX-1)

Preparation of 4-(3-ethoxy-1,2,2-trifluorobutyl)-2,2,3,3,5,5,6,6-octafluoromorpholine and 4,4'-(oxybis(1,2,2-trifluorobutane-3,1-diyl))bis(2,2,3,3,5,5,6,6-octafluoromorpholine)

A 600 mL Parr reactor was charged with diethyl ether (51.1 g, 689 mmol), MVA (50.2 g, 161 mmol), and TAPEH (3.2 g, 14 mmol). The reactor was then sealed and the resultant mixture was slowly heated to 75° C. After a 16 h stir, the reaction mixture was heated to 90° C. followed by a 0.5 h stir to consume any remaining initiator. After cooling to room temperature, GC analysis of the crude reaction material indicated 99% conversion of the MVA starting material. Single-plate distillation afforded 4-(3-ethoxy-1,2,2-trifluorobutyl)-2,2,3,3,5,5,6,6-octafluoromorpholine (143° C. at ambient pressure, 24.8 g, 40%) and 4,4'-(oxybis(1,2,2-trifluorobutane-3,1-diyl))bis(2,2,3,3,5,5,6,6-octafluoromorpholine) (143° C., 1.0 torr, 27.8 g, 25%). Analysis by GC-MS confirmed the presence of formation of 4-(3-ethoxy-1,2,2-trifluorobutyl)-2,2,3,3,5,5,6,6-octafluoromorpholine and 4,4'-(oxybis(1,2,2-trifluorobutane-3,1-diyl))bis(2,2,3,3,5,5,6,6-octafluoromorpholine).

Example 2(EX-2)

Preparation of 2,2,3,3,5,5,6,6-octafluoro-4-(1,2,2-trifluoro-3-methoxypropyl)morpholine and 4,4'-(oxybis(1,2,2-trifluoropropane-3,1-diyl))bis(2,2,3,3,5,5,6,6-octafluoromorpholine)

To a cooled (dry ice/acetone bath) 600 mL Parr reactor containing MVA (46.8 g, 150 mmol), TAPEH (2.0 g, 8.7 mmol), and tert-butanol (44.3 g, 598 mmol) was added dimethyl ether (39.8 g, 864 mmol). The reactor was then sealed and the resultant mixture was slowly heated to 75° C. After a 16 h stir, the reaction mixture was heated to 90° C. followed by a 0.5 h stir to consume any remaining initiator. After cooling to room temperature, the crude reaction mixture was washed with water (50 mL). The fluorous phase was collected and GC analysis indicated 65% conversion of the MVA starting material. Single-plate distillation afforded 2,2,3,3,5,5,6,6-octafluoro-4-(1,2,2-trifluoro-3-methoxypropyl)morpholine (142° C. at ambient pressure, 9.3 g, 17%) and 4,4'-(oxybis(1,2,2-trifluoropropane-3,1-diyl))bis(2,2,3,3,5,5,6,6-octafluoromorpholine) (91° C., 0.3 ton, 20.1 g, 20%). Analysis by GC-MS confirmed the formation of 2,2,3,3,5,5,6,6-octafluoro-4-(1,2,2-trifluoro-3-methoxypropyl)morpholine and 4,4'-(oxybis(1,2,2-trifluoropropane-3,1-diyl))bis(2,2,3,3,5,5,6,6-octafluoromorpholine).

Example 3(EX-3)

Preparation of 2,2,3,3,4,4,5,5-octafluoro-1-(1,2,2-trifluoro-3-(2,2,3,4,4,4-hexafluorobutoxy)propyl)pyrrolidine To a cooled (dry ice/acetone bath) 600 mL Parr reactor containing dimethyl ether (51.6 g, 1.12 mol) and TAPEH (5.5 g, 24 mmol) was slowly added hexafluoropropene (HFP, 28.6 g, 191 mmol). The internal reaction temperature was allowed to slowly rise to room temperature and was then slowly heated to 50° C. The internal pressure reached $1.38 \times 10^3$ kPa (200 psi). After a 16 h stir at the same temperature, the pressure dropped to 965 kPa (140 psi). The reactor was then heated to 80° C. and stirred for 0.5 h to consume any remaining initiator. After cooling to room temperature, the crude reaction material was purified via single-plate distillation to afford 1,1,1,2,3,3-hexafluoro-4-methoxybutane (80.6° C. at ambient pressure, 31.6 g, 85%).

A 300 mL Parr reactor was charged with 1,1,1,2,3,3-hexafluoro-4-methoxybutane (10.5 g, 53.5 mmol), Pf vinyl pyrrolidine (16.4 g, 55.6 mmol), and tBuOOtBu (0.6 g, 4.0 mmol). The reactor was then sealed and the resultant mixture was slowly heated to 125° C. After a 16 h stir, the reaction mixture was heated to 160° C. followed by a 0.5 h stir to consume any remaining initiator. After cooling to room temperature, GC analysis indicated 3% conversion of the 1,1,1,2,3,3-hexafluoro-4-methoxybutane starting material to 2,2,3,3,4,4,5,5-octafluoro-1-(1,2,2-trifluoro-3-(2,2,3,4,4,4-hexafluorobutoxy)propyl)pyrrolidine. Analysis by GC-MS confirmed the formation of 2,2,3,3,4,4,5,5-octafluoro-1-(1,2,2-trifluoro-3-(2,2,3,4,4,4-hexafluorobutoxy)propyl)pyrrolidine.

Example 4(EX-4)

Preparation of 2,2,3,3,5,5,6,6-octafluoro-4-(1,2,2-trifluoro-3-((3,3,4,5,5,5-hexafluoropentan-2-yl)oxy)butyl)morpholine A 600 mL Parr reactor was charged with diethyl ether (110 g, 1.5 mol) and TAPEH (4.3 g, 18.8 mmol). The reactor was sealed and heated to 75° C. followed by the slow addition of HFP (56.3 g, 375 mmol). After complete addition of HFP, the mixture was allowed to stir for 16 h before heating to 90° C. to consume any remaining initiator (TAPEH). After 0.5 h, the reaction mixture was allowed to cool to room temperature. The resultant crude reaction mixture was subjected to single plate distillation (115° C. at ambient pressure) to afford 4-ethoxy-1,1,1,2,3,3-hexafluoropentane (22.5 g, 27%) as a colorless liquid.

A 300 mL Parr reactor was charged with 4-Ethoxy-1,1,1,2,3,3-hexafluoropentane (10.1 g, 45.1 mmol), MVA (14.4 g, 46.3 mmol), and tBuOOtBu (0.6 g, 4.0 mmol). The reactor was then sealed and the resultant mixture was slowly heated to 125° C. After a 16 h stir, the reaction mixture was heated to 160° C. followed by a 0.5 h stir to consume any remaining initiator. After cooling to room temperature, GC analysis indicated 4.5% conversion of the 4-Ethoxy-1,1,1,2,3,3-hexafluoropentane starting material to 2,2,3,3,5,5,6,6-octafluoro-4-(1,2,2-trifluoro-3-((3,3,4,5,5,5-hexafluoropentan-2-yl)oxy)butyl)morpholine. Analysis by GC-MS confirmed the formation of 2,2,3,3,5,5,6,6-octafluoro-4-(1,2,2-trifluoro-3-((3,3,4,5,5,5-hexafluoropentan-2-yl)oxy)butyl)morpholine.

Example 5(EX-5)

Preparation of 4-(3-ethoxy-1,2-difluoro-2-(trifluoromethyl)butyl)-2,2,3,3,5,5,6,6-octafluoromorpholine and 4,4'-(oxybis(1,2-difluoro-2-(trifluoromethyl)butane-3,1-diyl))bis(2,2,3,3,5,5,6,6-octafluoromorpholine)

To a 600 mL Parr reactor was charged diethyl ether (60.4 g, 815 mmol), M-1P (73.5 g, 204 mmol), and TAPEH (4.1 g, 18 mmol). The reactor was then sealed and the resultant mixture was slowly heated to 75° C. After a 16 h stir, the reaction mixture was heated to 90° C. followed by a 0.5 h stir to consume any remaining initiator. After cooling to room temperature, GC analysis of the crude reaction material indicated 35% conversion of the M-1P starting material and a product ratio of 1:1 4-(3-ethoxy-1,2-difluoro-2-(trifluoromethyl)butyl)-2,2,3,3,5,5,6,6-octafluoromorpholine: 4,4'-(oxybis(1,2-difluoro-2-(trifluoromethyl)butane-3,1-diyl))bis(2,2,3,3,5,5,6,6-octafluoromorpholine). Analysis by GC-MS confirmed the formation of 4-(3-ethoxy-1,2-difluoro-2-(trifluoromethyl)butyl)-2,2,3,3,5,5,6,6-octafluoromorpholine and 4,4'-(oxybis(1,2-difluoro-2-(trifluoromethyl)butane-3,1-diyl))bis(2,2,3,3,5,5,6,6-octafluoromorpholine)

Foreseeable modifications and alterations of this invention will be apparent to those skilled in the art without departing from the scope and spirit of this invention. This invention should not be restricted to the embodiments that are set forth in this application for illustrative purposes. To the extent that there is any conflict or discrepancy between this specification as written and the disclosure in any document mentioned or incorporated by reference herein, this specification as written will prevail.

What is claimed is:

1. A acyclic fluorinated compound of formula (I)

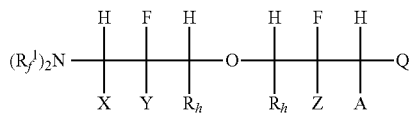

where:
each $R_h$ is independently H or $CH_3$;
X is selected from F or $CF_3$, and Y is selected from H, F, or $CF_3$, wherein when X is $CF_3$ then Y is F and when Y is $CF_3$ then X is F;
each $R_f^1$ is independently selected from a linear or branched perfluorinated alkyl group comprising 1-8 carbon atoms and optionally comprising at least one catenated atom selected from O, N, or combinations thereof; or the two $R_f^1$ groups are bonded together to form a fluorinated ring structure comprising 4-8 carbon atoms and optionally comprising at least one catenated atom selected from O, N, or combinations thereof;
A is selected from F, or $CF_3$;
Z is selected from H, F or $CF_3$; and
Q is selected from (i) a F atom, (ii) a Cl atom, (iii) a linear, cyclic, or branched perfluorinated alkyl group comprising 1-8 carbon atoms and optionally comprising at least one catenated atom selected from O, N, or combinations thereof, or (iv) a $G(R_f^2)_e$ group, where G is an O atom or a N atom wherein:
when Q is a Cl atom, then Z and A are F atoms;
when G is O then e is 1, Z is H, F or $CF_3$; A is F; and $R_f^2$ is a linear or branched perfluorinated alkyl group comprising 1-10 carbon atoms and optionally comprising at least one catenated atom selected from O, N, or combinations thereof;
when G is N then e is 2, and each $R_f^2$ group is independently a linear or branched perfluorinated alkyl group comprising 1-8 carbon atoms and optionally comprising at least one catenated atom selected from O, N, or combinations thereof or the two $R_f^2$ groups are bonded together to form a fluorinated ring structure comprising 4-8 carbon atoms and optionally comprising at least one catenated atom selected from O, N, or combinations thereof, with the proviso that when A is $CF_3$ then Z is F, and when Z is $CF_3$ then A is F.

2. The acyclic fluorinated compound of claim 1, wherein $Q = N(R_f^1)_2$.

3. The acyclic fluorinated compound of claim 2, wherein $N(R_f^1)_2$ is a perfluorinated morpholine group.

4. The acyclic fluorinated compound of claim 1, wherein Q is a perfluorinated alkyl group comprising less than 4 carbon atoms.

5. The acyclic fluorinated compound of claim 1, wherein X and Y are both F.

6. The acyclic fluorinated compound of claim 1, wherein A and Z are both F.

7. The acyclic fluorinated compound of claim 1, wherein the acyclic fluorinated compound comprises at least one of the following:

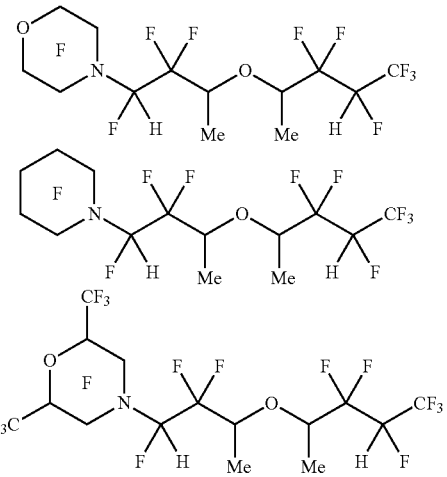

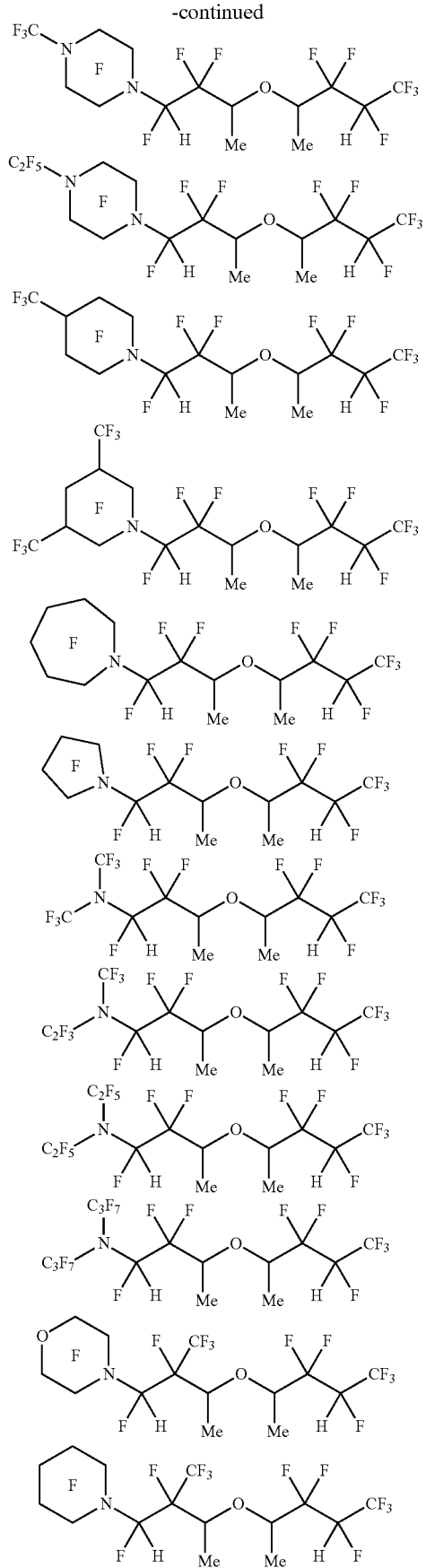
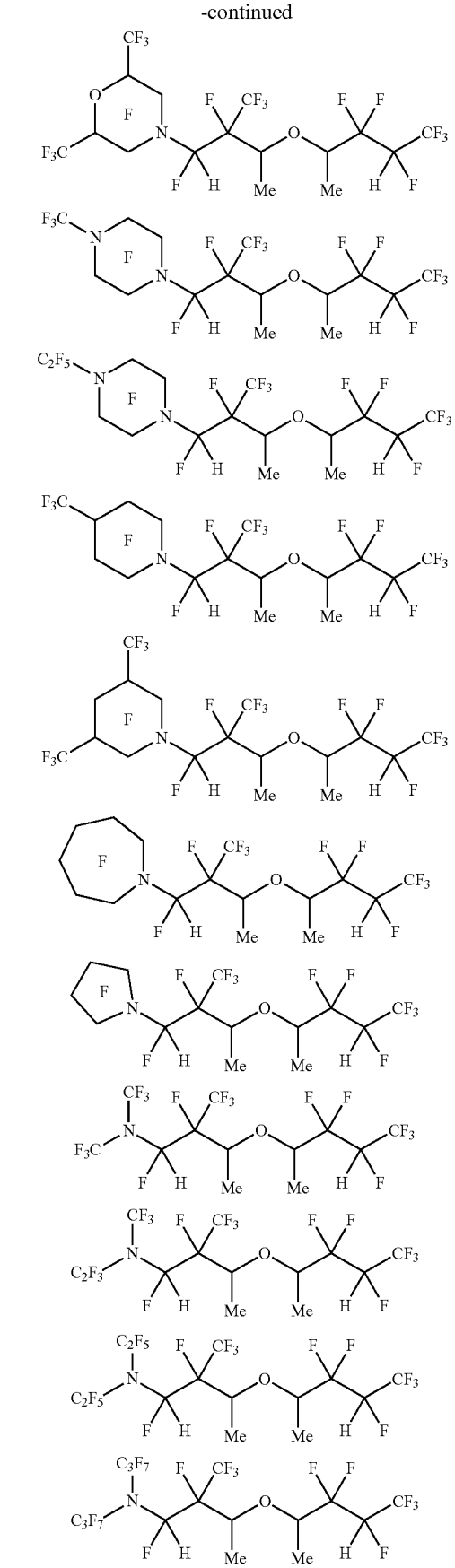

-continued
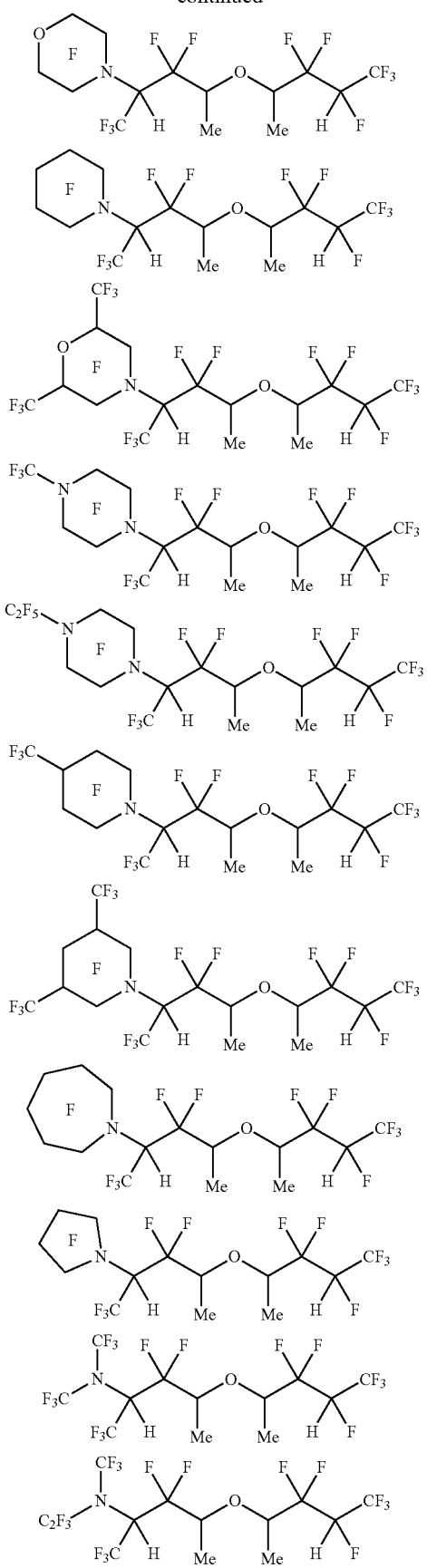
-continued
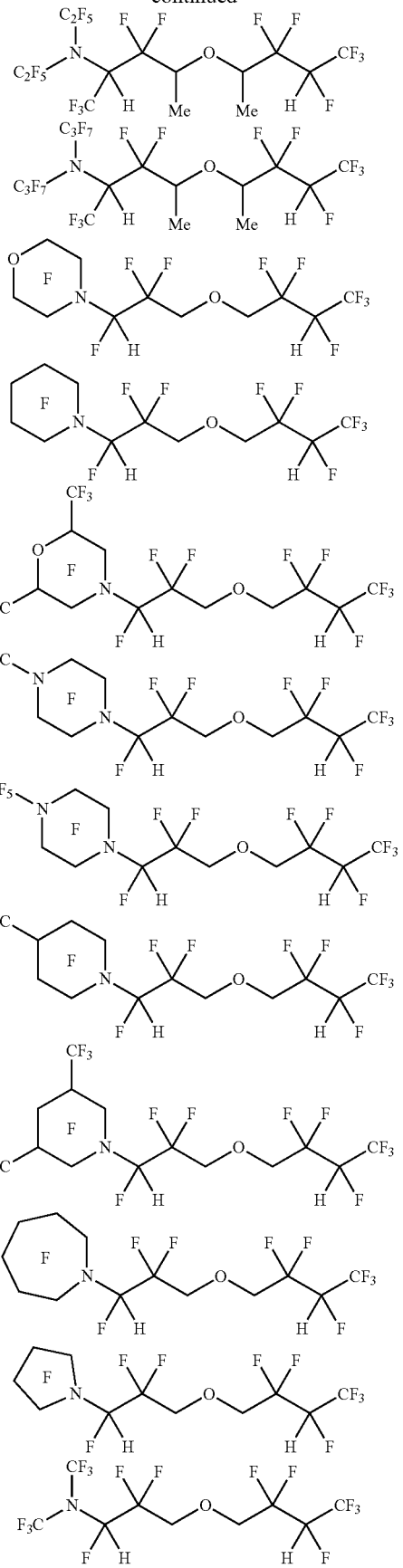

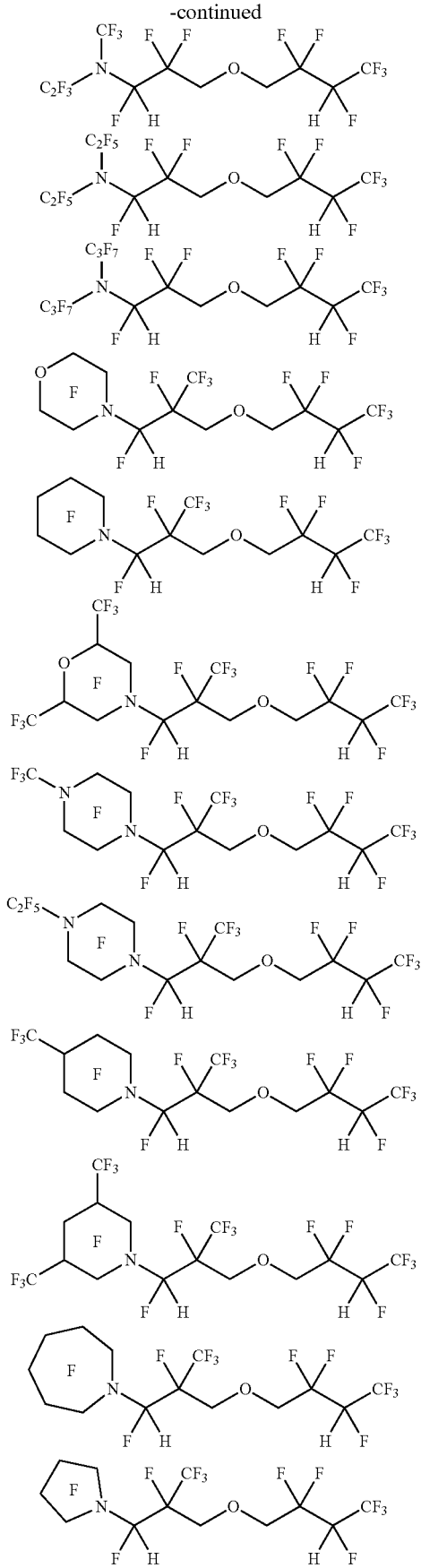
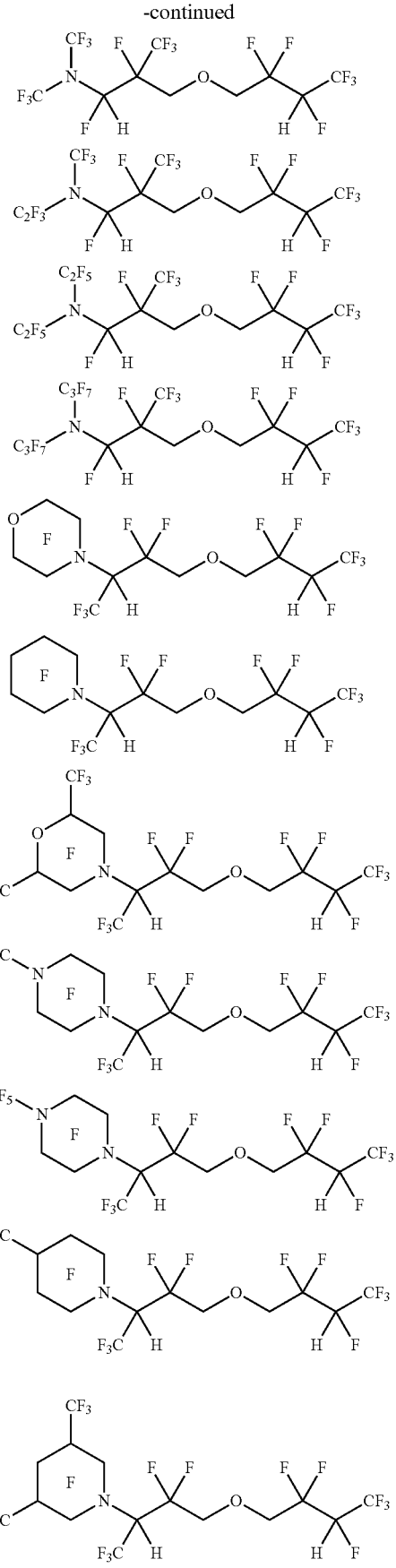

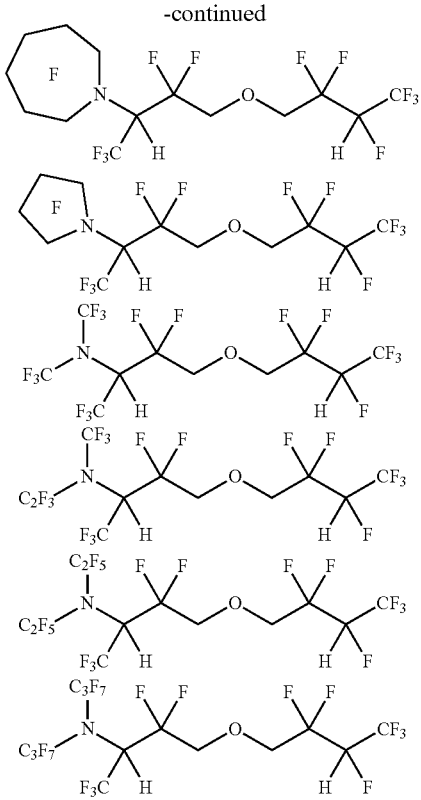

where Me refers to a methyl group.

8. A working fluid comprising the acyclic fluorinated compound according to claim 1, wherein the acyclic fluorinated compound is present in the working fluid in an amount of at least 25% by weight based on the total weight of the working fluid.

9. A composition comprising a purified form of the acyclic fluorinated compound according to claim 1.

10. The acyclic fluorinated compound of claim 1, wherein the acyclic fluorinated compound has a global warming potential of less than 100.

11. A working fluid comprising the acyclic fluorinated compound according to claim 1, wherein the acyclic fluorinated compound is present in the working fluid in an amount of at least 25% by weight based on the total weight of the working fluid.

12. The working fluid of claim 11, wherein the working fluid further comprises a co-solvent.

13. An apparatus for heat transfer comprising a mechanism for transferring heat to or from a device, the mechanism comprising a heat transfer fluid that comprises the acyclic fluorinated compound according to claim 1.

14. An apparatus for heat transfer according to claim 13, wherein the device is selected from a microprocessor, a semiconductor wafer used to manufacture a semiconductor device, a power control semiconductor, an electrochemical cell, an electrical distribution switch gear, a power transformer, a circuit board, a multi-chip module, a packaged or unpackaged semiconductor device, a fuel cell, and a laser.

15. An apparatus according to claim 13, wherein the mechanism for transferring heat is a component in a system for maintaining a temperature or temperature range of an electronic device.

16. An apparatus according to claim 13, wherein the device comprises a soldered electronic component.

17. An apparatus according to claim 13, wherein the mechanism comprises vapor phase soldering.

* * * * *

UNITED STATES PATENT AND TRADEMARK OFFICE
CERTIFICATE OF CORRECTION

PATENT NO. : 10,344,006 B2
APPLICATION NO. : 16/073854
DATED : July 9, 2019
INVENTOR(S) : Sean Smith Page 1 of 2

It is certified that error appears in the above-identified patent and that said Letters Patent is hereby corrected as shown below:

In the Specification

Column 11,
Lines 54-58, delete " 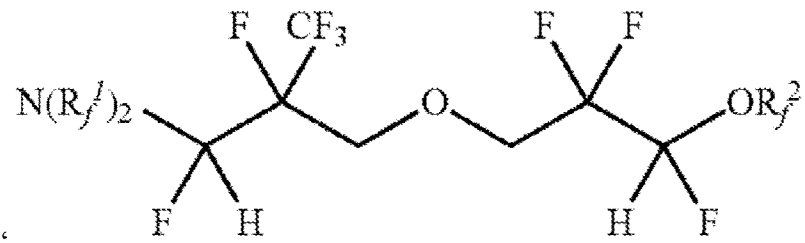 " and insert -- 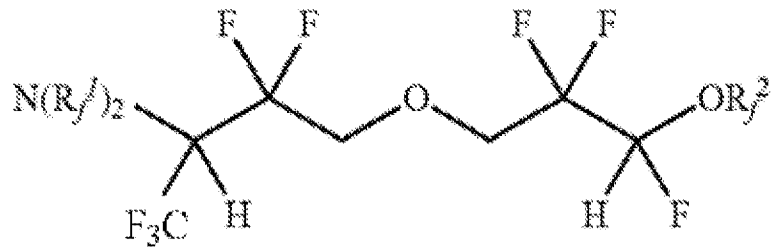 --, therefor.

Column 20,
Lines 12-16, delete " $\frac{\int_0^{iTH} a_i C_{oi} e - t/\tau_i dt}{\int_0^{iTH} a_{CO_2} [C_{CO_2}(t)] dt}$ " and insert -- $\frac{\int_0^{iTH} a_i C_{oi} e^{-t/\tau_i} dt}{\int_0^{iTH} a_{CO_2} [C_{CO_2}(t)] dt}$ --, therefor.

Column 20,
Line 18, delete "a," and insert -- $a_i$ --, therefor.

Signed and Sealed this
Tenth Day of September, 2019

Andrei Iancu
*Director of the United States Patent and Trademark Office*

CERTIFICATE OF CORRECTION (continued)
U.S. Pat. No. 10,344,006 B2

In the Claims

Column 47,
Line 66, in Claim 1, delete "$CF_3$then" and insert -- $CF_3$ then --, therefor.
Line 67, in Claim 1, delete "$CF_3$then" and insert -- $CF_3$ then --, therefor.